US011633600B2

(12) United States Patent
Libbus et al.

(10) Patent No.: US 11,633,600 B2
(45) Date of Patent: Apr. 25, 2023

(54) TITRATION ASSIST SYSTEM

(71) Applicant: LivaNova USA, Inc., Houston, TX (US)

(72) Inventors: Imad Libbus, St. Paul, MN (US); Bruce KenKnight, Maple Grove, MN (US); Scott Stubbs, Maple Grove, MN (US); Scott Mazar, Maple Grove, MN (US)

(73) Assignee: LivaNova USA, Inc., Houston, TX (US)

( * ) Notice: Subject to any disclaimer, the term of this patent is extended or adjusted under 35 U.S.C. 154(b) by 0 days.

(21) Appl. No.: 17/136,804

(22) Filed: Dec. 29, 2020

(65) Prior Publication Data

US 2022/0203095 A1     Jun. 30, 2022

(51) Int. Cl.
*A61N 1/36* (2006.01)
(52) U.S. Cl.
CPC ...... *A61N 1/36114* (2013.01); *A61N 1/36139* (2013.01); *A61N 1/36175* (2013.01)
(58) Field of Classification Search
CPC ............... A61N 1/36114; A61N 1/36139
USPC ............................................. 607/9
See application file for complete search history.

(56) References Cited

U.S. PATENT DOCUMENTS

| | | |
|---|---|---|
| 9,770,599 B2 | 9/2017 | Libbus et al. |
| 9,950,169 B2 | 4/2018 | Libbus et al. |
| 2013/0013015 A1 | 1/2013 | Takata |
| 2013/0030496 A1 | 1/2013 | Karamanoglu et al. |
| 2016/0082259 A1 | 3/2016 | McCabe et al. |
| 2019/0126045 A1 | 5/2019 | Libbus et al. |

OTHER PUBLICATIONS

International Search Report and Written Opinion on PCT Appl. Ser. No. PCT/US2021/065283 dated Mar. 29, 2022 (11 pages).

*Primary Examiner* — Nadia A Mahmood
(74) *Attorney, Agent, or Firm* — Foley & Lardner LLP

(57) ABSTRACT

A neurostimulation system comprises a sensor and a control system. The sensor is configured to detect a cardiac physiological measure of a patient. The control system is programmed to monitor, via the sensor, the cardiac physiological measure during the treatment. The control system is further programmed to detect a change in the cardiac physiological measure during the treatment. The control system is further programmed to determine, based on the detected change in the cardiac physiological measure, a first transition time in a duty cycle of a neurostimulation signal delivered to the patient where the neurostimulation signal transitions between a stimulation OFF period and a stimulation ON period.

20 Claims, 18 Drawing Sheets

TITRATION ASSIST SYSTEM

BACKGROUND

Autonomic regulation neurostimulation therapy delivered by vagus nerve stimulation ("VNS") is a treatment for congestive heart failure. VNS therapy commonly requires implantation of a neurostimulator, which, when activated, applies or delivers a stimulation signal to the vagus nerve of a patient. A vagus nerve stimulation signal is typically a periodic current pulse signal defined by an output current amplitude or intensity. Following implantation and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under the control of a physician with the patient given time between successive increases in VNS therapy intensity to adapt to the new intensity. As stimulation is chronically applied at each new intensity level, the patient's side effect threshold gradually increases, allowing for an increase in intensity during subsequent titration sessions.

SUMMARY

One embodiment relates to a neurostimulation system comprising a sensor and a control system. The sensor is configured to detect a cardiac physiological measure of a patient. The control system is programmed to monitor, via the sensor, the cardiac physiological measure during a treatment. The control system is further programmed to detect a change in the cardiac physiological measure during the treatment. The control system is further programmed to determine, based on the detected change in the cardiac physiological measure, a first transition time in a duty cycle of a neurostimulation signal delivered to the patient where the neurostimulation signal transitions between a stimulation OFF period and a stimulation ON period.

Another embodiment relates to a method of delivering a neurostimulation signal to a patient from an implantable pulse generator. The method comprises delivering, by the implantable pulse generator, a neurostimulation signal to the patient via an electrode assembly, the neurostimulation signal having a duty cycle with a stimulation ON period and a stimulation OFF period. The method further comprises detecting, by a sensor, a cardiac physiological measure of the patient. The method further comprises monitoring, by a control system, the cardiac physiological measure during a treatment via the sensor. The method further comprises detecting, by the control system, a change in the cardiac physiological measure during the treatment. The method further comprises determining, by the control system based on the detected change in the cardiac physiological measure, a first transition time in the duty cycle where the neurostimulation signal transitions between the stimulation OFF period and the stimulation ON period.

Another embodiment relates to one or more non-transitory computer-readable mediums including instructions executable by one or more processors. The instructions are executable by the one or more processors to detect, via a sensor, a cardiac physiological measure of a patient. The instructions are further executable by the one or more processors to monitor, via the sensor, the cardiac physiological measure during a treatment. The instructions are further executable by the one or more processors to detect a change in the cardiac physiological measure during the treatment. The instructions are further executable by the one or more processors to determine, based on the detected change in the cardiac physiological measure, a first transition time in a duty cycle of a neurostimulation signal delivered to the patient where the neurostimulation signal transitions between a stimulation OFF period and a stimulation ON period based on the detected change in the cardiac physiological measure.

BRIEF DESCRIPTION OF THE DRAWINGS

Further features, characteristics, and advantages of the present disclosure will become apparent to a person of ordinary skill in the art from the following detailed description of embodiments of the present disclosure, made with reference to the drawings annexed, in which like reference characters refer to like elements.

DETAILED DESCRIPTION

Figure 1:
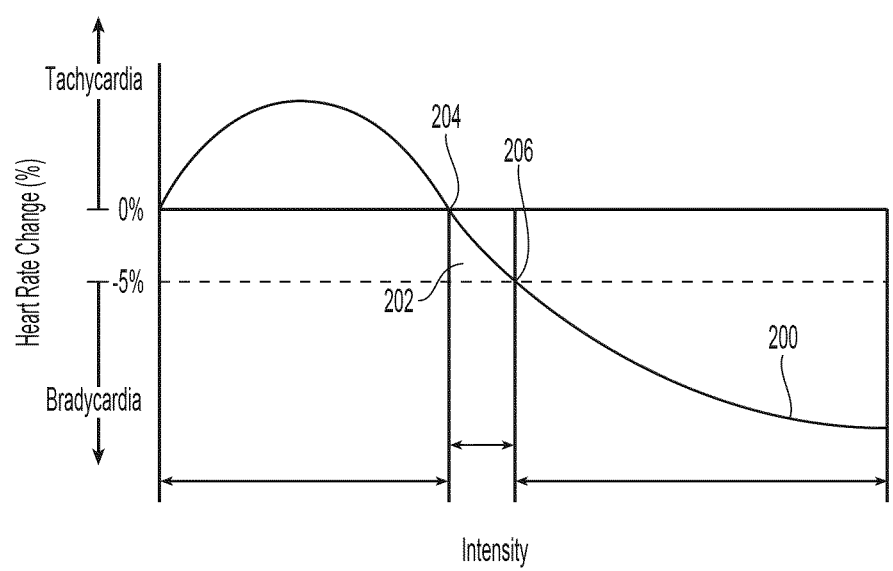
FIG. 1 is an illustrative graphic of a heart rate change response as a function of stimulation signal intensity, according to an exemplary embodiment.

When delivering neurostimulation therapies to patients, it is generally desirable to avoid stimulation intensities that result in either excessive tachycardia or excessive bradycardia side effects. The neurostimulator may be adjusted to deliver varying stimulation intensities to the patient. To find a beneficial therapeutic level of neurostimulation, researchers have utilized the patient's heart rate changes. Some researchers have proposed that heart rate reduction serves as a functional response indicator or surrogate for effective recruitment of nerve fibers and engagement of the autonomic nervous system elements, which may be indicative of therapeutic levels of vagus nerve stimulation.

A therapeutic level or dose of vagus nerve stimulation that results in a heart rate reduction of up to 5% has been described as treatment that is delivered within the desired "neural fulcrum zone." The neural fulcrum zone corresponds to a combination of stimulation parameters at which autonomic engagement is achieved but for which a functional response determined by heart rate change is nullified due to the competing effects of afferently and efferently-transmitted action potentials. In this way, the tachycardia-inducing stimulation effects are offset by the bradycardia-inducing effects, thereby minimizing side effects, such as significant heart rate changes, while providing a therapeutic level of stimulation.

Accordingly, to determine whether a particular neurostimulation therapy is effectively providing a therapeutic level or dose to the patient, monitored ECG data can be synchronized with a stimulation delivery schedule of the neurostimulation therapy and associated with either a stimulation ON period of the neurostimulation therapy or a stimulation OFF period of the neurostimulation therapy. This monitored ECG data from the stimulation ON period and the stimulation OFF period may then be compared to analyze various aspects of the neurostimulation therapy provided to the patient (e.g., to determine whether the neurostimulation therapy elicits a cardiac response within the neural fulcrum zone).

Traditionally, synchronizing the monitored ECG data with the stimulation delivery schedule of the neurostimulation therapy has required the use of a transmission detection cable to detect telemetry programming signals transmitted between an external programming wand and a neurostimulator implanted within the patient. The detected telemetry programming signals are generally used to determine the stimulation delivery schedule and to identify various aspects of the programmed neurostimulation therapy. For example, from the detected telemetry programming signals, the stimulation ON period and the stimulation OFF period can be identified, and the monitored ECG data can be synchronized accordingly.

However, the systems and methods described herein beneficially allow for the synchronization of monitored ECG data with a stimulation delivery schedule of an implanted neurostimulator without the use of a transmission detection cable. For example, the systems and methods described herein utilize monitored ECG data captured from the patient in combination with various known stimulation parameters to inferentially determine a stimulation delivery cycle of the neurostimulation therapy. Specifically, the systems and methods described herein allow for the inferential identification of the stimulation ON period and the stimulation OFF period of the neurostimulation therapy. As such, the monitored ECG data is synchronized and/or associated with either the stimulation ON period or the stimulation OFF period, based on the determined stimulation delivery cycle of the neurostimulation therapy, to allow for the various aspects of the neurostimulation to be effectively analyzed.

Because the systems and methods allow for the inferential determination of the stimulation delivery schedule of the neurostimulator, the traditional transmission detection cable may be completely omitted from the systems and methods described herein. This omission of the transmission detection cable may be beneficial for a variety of reasons. For example, transmission detection cables are traditionally expensive to manufacture and prone to breaking. Additionally, a transmission detection cable must be properly placed on the external programming wand to function as intended (e.g., effectively detect the telemetry signals of the external programming wand). Further, use of a transmission detection cable generally requires the user to perform a programming event on the neurostimulator in order to synchronize the monitored ECG data with the neurostimulation, even in the case that the stimulation parameters of the neurostimulation will be unchanged. Accordingly, by allowing for the omission of the transmission detection cable, the systems and methods described herein effectively reduce the overall cost of associated systems, eliminate the need for proper placement of the transmission detection cable on the external programming wand, and allow for the synchronization of the monitored ECG data with the neurostimulation provided by the neurostimulator without the need to perform a programming event.

Shown in FIG. 1 is a graphic illustration of the neural fulcrum zone and heart rate change response as a function of increasing vagus nerve stimulation signal intensity and constant frequency. The x-axis represents the intensity level of the stimulation signal, and the y-axis represents the observed heart rate change from the patient's baseline basal heart rate observed when no stimulation is delivered. The patient's heart rate change response 200 is depicted as depending on the stimulation signal intensity. As the intensity (e.g., output current amplitude) is increased, a tachycardia zone is observed. This response 200 is more or less pronounced depending on the other stimulation parameters. As the intensity continues to be increased, the patient's heart rate change response 200 begins to decrease and eventually enters a bradycardia zone. The neural fulcrum zone is depicted as the response zone 202 between no heart rate change 0% (occurring at point 204) and a heart rate reduction of 5% (occurring at point 206).

In vagus nerve stimulation therapy, the titration process can take up to 10-12 weeks before a full therapeutic dosage can even be tolerated. In order to reduce or minimize the titration process time to a full therapeutic dose, it is desirable to monitor the physiological response to evaluate whether the applied stimulus dosage in the titration process is effective without inducing undesirable side effects. Accordingly, there remains a need for systems and methods to assess autonomic engagement response to delivery of a vagus nerve stimulation signal.

Figure 2A:
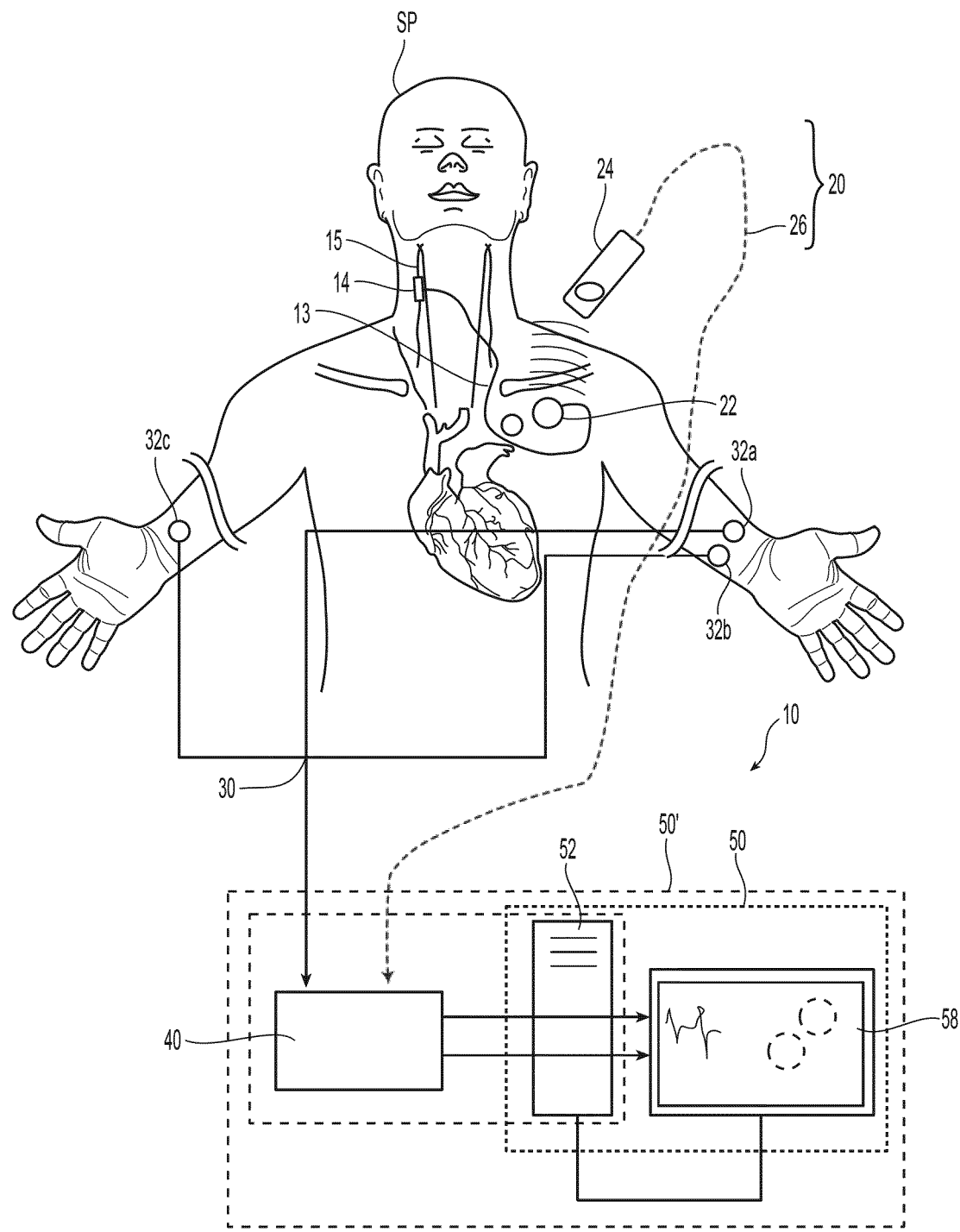
FIG. 2A is a schematic view of a system for assessing vagus nerve stimulation from an implanted neurostimulator for treatment of congestive heart failure ("CHF"), according to an exemplary embodiment.

Shown in FIG. 2A (and similarly in FIG. 2B) is a system 10 for monitoring and assessing a physiological response of a subject patient SP to neurostimulation therapy and, in particular, for monitoring and assessing heart rate dynamic response to vagus nerve stimulation for the treatment of CHF, according to an exemplary embodiment. In various embodiments, the system 10 provides one or more indicators to a patient and/or clinician of the effectiveness of a delivered stimulation treatment by indicating autonomic engagement in the subject patient SP in a timeframe that is real-time, which includes a timeframe that is instantaneous, immediate, sequential, or proximate to a parameter change; encompassing a titration session; and/or within one minute, ten minutes, and/or an hour of a stimulation parameter change. In some embodiments, the one or more real-time indicators of the effectiveness of a delivered stimulation treatment allow and/or facilitate the modification of the stimulation therapy, the subject patient SP's advancement through the titration process, and/or the delivery of effective levels of therapy to the subject patient SP in a timeframe that is real-time, which includes a timeframe that is instantaneous, immediate, sequential, or proximate to a parameter change; encompassing a titration session; and/or within one minute, ten minutes, and/or an hour of a stimulation parameter change. Alternatively or additionally, the titration process can be automatically altered or increased in intensity with the detection, monitoring, and/or measurement by the system 10 occurring in real-time. The assessment can be read from system 10 in real-time, or, if needed or desired, the assessment can be read from the system 10 by a clinician at a later time in a clinic or other environment.

The system 10 captures the physiological response to the vagus nerve stimulation. In some embodiments, the system 10 (i) detects the electrical heart activity response, e.g., electrocardiogram ("ECG") of the subject patient SP in response to the vagus nerve stimulation; (ii) determines the change in heart rate dynamics in response to the stimulation; and (iii) visually displays the change in heart rate dynamics in a manner that indicates the extent of autonomic engagement in response to the delivered stimulus. By providing the indication of autonomic engagement in real-time, the effectiveness of the stimulus treatment can be assessed by the patient or clinician, and the stimulus can be adjusted as needed in real-time to ensure delivery of an effective stimulus or the delivery of a stimulus that advances the titration of the subject patient SP to an effective stimulus. Moreover, by assessing a stimulation signal of a titration process in real-time, the stimulation signal can be optimized and the overall titration process and the therapy can be made more efficient by minimizing the time required to achieve a titrated delivery of a full therapeutic dose or intensity of a vagus nerve stimulus.

In some embodiments, the system 10 includes a first interface or communication assembly 20 for communication with a stimulation delivery device 22 and a second interface assembly 30 for capturing the physiological response of the subject patient SP. In some instances, various components (e.g., a wand transmission detection cable 26) of the first interface 20 may be omitted, as will be described further below. In some embodiments, the second interface assembly 30 captures data suitable for generating the ECG waveform of the subject patient SP to the stimulation delivery. In various embodiments, as shown in FIG. 2A, the stimulation delivery device 22 is embodied as an implantable medical device ("IMD") and, more particularly, an implantable neurostimulator 22. Embodiments of the neurostimulator 22 are shown and described in U.S. Pat. Nos. 9,770,599 and 9,950,169, each of which is incorporated by reference in its entirety. As described in the cited patent documents, the implantable medical device includes a pulse generator 22, a lead 13, and electrodes 14 for delivering a pulse generated stimulus about a vagus nerve 15 of the subject patient SP. A commercially available embodiment of the implantable neurostimulator 22 includes the VITARIA™ Model 7103 Pulse Generator from Livallova USA, Inc. of Houston, Tex., USA.

Figure 3:
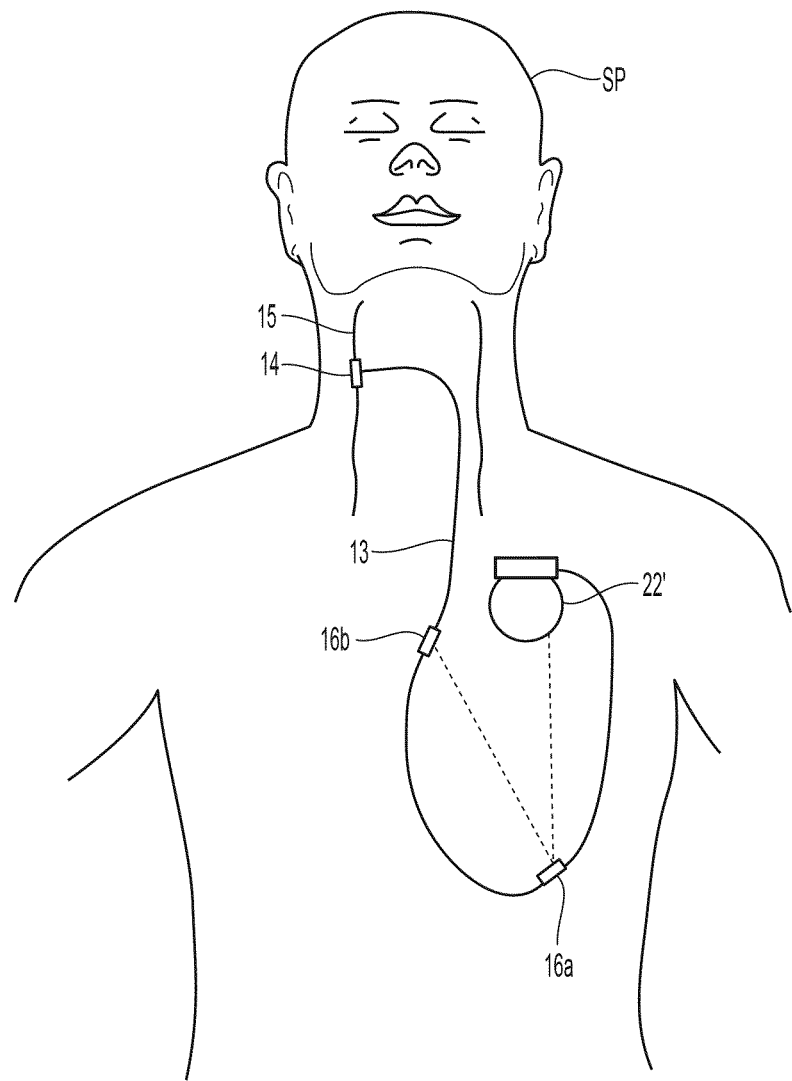
FIG. 3 is another schematic view of a neurostimulator for use in the system of FIG. 2A, according to an exemplary embodiment.

Shown in FIG. 3 is another embodiment of a neurostimulator 22', for use with the assessment system 10, which includes or incorporates an implantable cardioverter-defibrillator ("ICD"). An implantable VNS/ICD system is also shown and described in U.S. Pat. No. 9,770,599, which is incorporated by reference in its entirety. An embodiment of an implantable VNS/ICD system includes a pulse generation module with a control system, a VNS subsystem, and an ICD subsystem. A first electrode assembly 14 is coupled to the pulse generation module and includes a VNS electrode configured to couple to the vagus nerve 15. A second electrode assembly 16a, 16b is coupled to the pulse generation module and includes a subcutaneous electrode. Another embodiment of an implantable VNS/ICD system includes a primary pulse generation module having a primary control system and an ICD subsystem and a secondary pulse generation module having a secondary control system and a VNS subsystem. The secondary pulse generation module is placed in data communication with the primary pulse generation module, with the second electrode assembly 16a, 16b coupled to the primary pulse generation module, in which the second electrode assembly 16a, 16b includes a subcutaneous electrode. Another electrode assembly is coupled to the secondary pulse generation module. This electrode assembly includes a VNS electrode 14 configured to couple to the vagus nerve 15. In various embodiments, the implantable VNS/ICD system is configured to deliver a chronic VNS therapy to the vagus nerve 15 with a VNS subsystem of a pulse generation module. In response to detection of a cardiac event, the implantable VNS/ICD system is configured to deliver electrical cardioversion-defibrillation energy with an ICD subsystem of the pulse generation module.

Figure 2B:
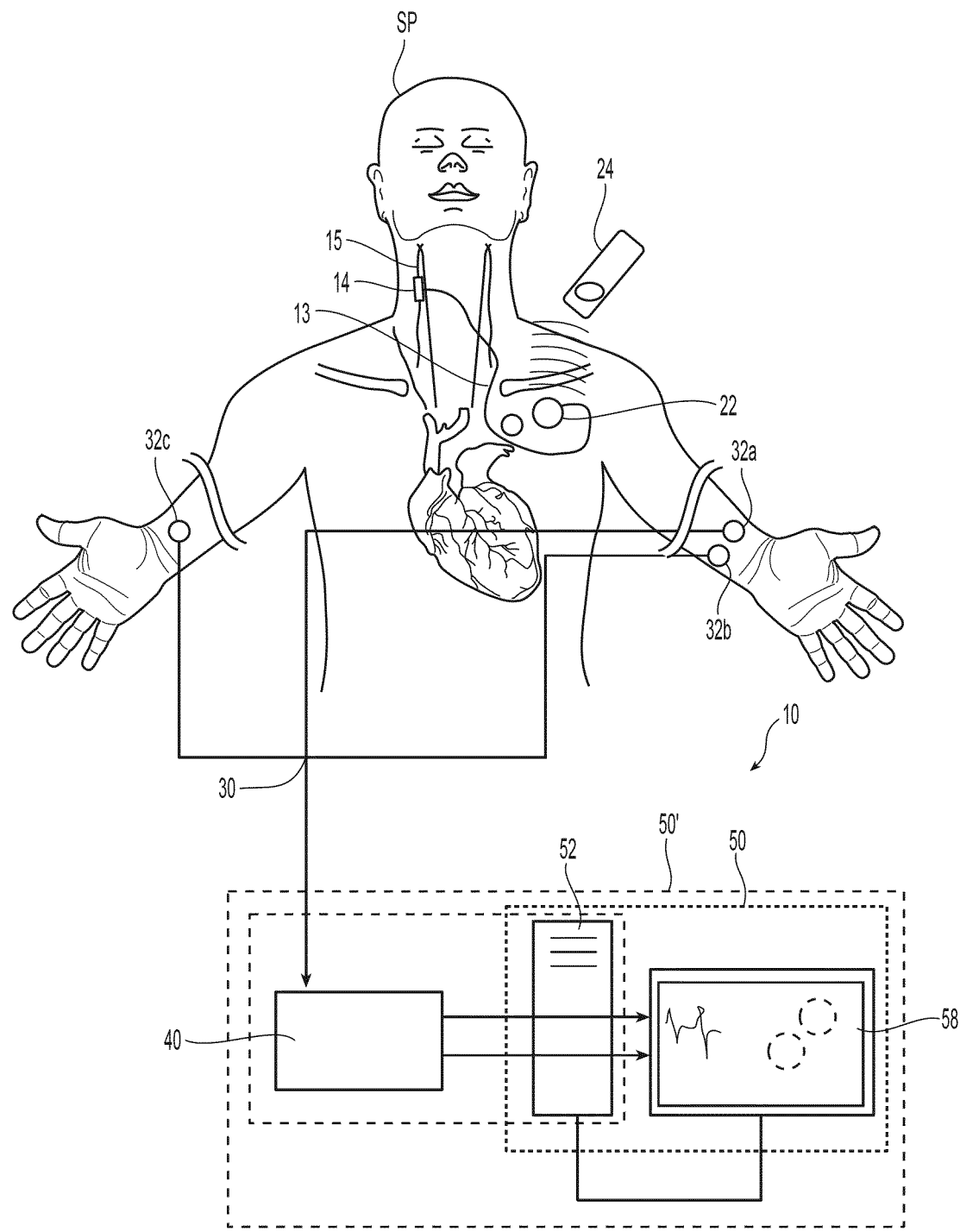
FIG. 2B is another schematic view of the system of FIG. 2A, shown without a transmission detection cable, according to an exemplary embodiment.

Referring to FIGS. 2A and 2B, a computer processing device 50 may be coupled with the first and second interfaces 20, 30 (as shown in FIG. 2A) or with only the second interface 30 (as shown in FIG. 2B) for processing the captured ECG-suitable signal to determine, for example, in real-time, the heart rate dynamics in the subject patient SP in response to delivery of the stimulation signal to the vagus nerve 15. The ECG-suitable signal captured by the second interface 30 allows the determination and display of a periodic waveform with repeating "cardiac cycles" as shown, for example, in FIG. 15. A "cardiac cycle" may refer to one complete PQRSTU interval of the patient's heart functioning, ending with the P wave of the next succeeding cardiac cycle. An "interbeat interval" may refer to the time period between a predetermined point in a first cardiac cycle of the patient and the same predetermined point in the immediately succeeding cardiac cycle of the patient. Examples of interbeat intervals include an R-R interval, a P-P interval, or a T-T interval. Interbeat intervals may include a single interval or a moving average (either simple or weighted) of several consecutive intervals. Within a single cardiac cycle, a "cardiac period" is a length of time between a first point in the cardiac cycle of the patient and a second, later point. An exemplary cardiac period includes a P-wave, a Q-wave, an R-wave, an S-wave, a QRS complex, a T-wave, and a U-wave of the cardiac cycle, which can be readily identified by electrocardiography or other techniques of monitoring the electrical activity of the heart. For example, the R-wave presents the maximum amplitude of the cardiac cycle. In some instances, various other heart rate dynamics may additionally be determined and/or monitored, such as a P-R interval, a Q-T interval, heart rate variability, and/or any other suitable heart rate dynamics, as necessary for a given application.

According to one embodiment of the processing of the ECG-suitable signal described herein, the heart rate dynamics are determined from an R-R interbeat interval analysis of the cardiac period QRS complex in the ECG waveform. From the heart rate dynamics, the computer processing device 50 displays in real-time an indication of autonomic engagement in the subject in response to the stimulus. The R-R interval analysis provides a desired resolution in the ECG waveform from which to determine and indicate the autonomic response in real-time.

Figure 4A:
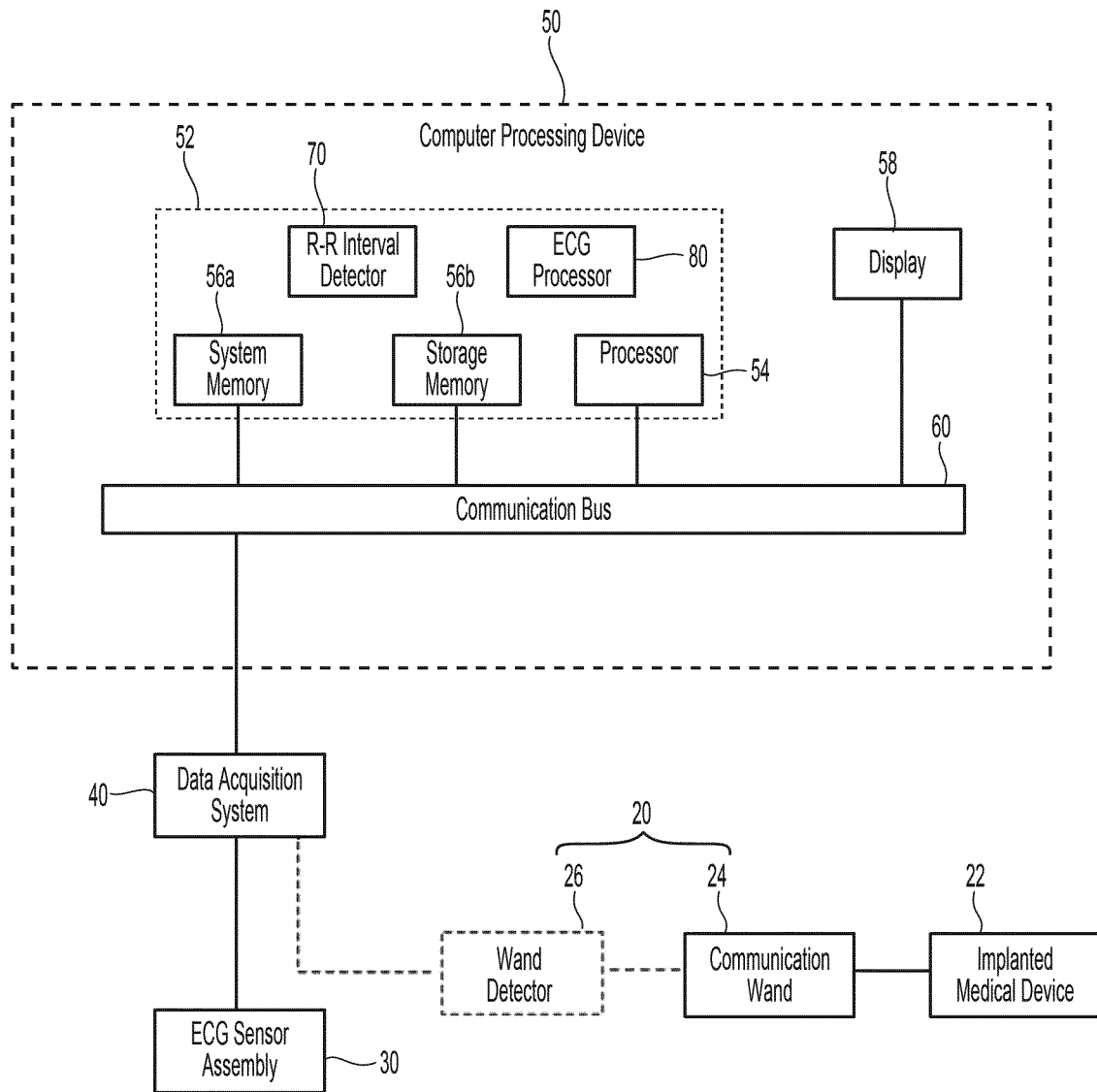
FIG. 4A is a schematic view of components of the system of FIG. 2A, according to an exemplary embodiment.

Referring now to FIG. 4A, another schematic view of the system 10 with the computer processing device 50 for assessing a vagus nerve stimulation treatment is shown, according to an exemplary embodiment. The computer processing device 50 includes processing hardware 52, such as, for example, a central processing unit 54 and associated memory or computer readable medium (e.g., system memory 56a and storage memory 56b), for processing ECG-suitable signals in a manner as described herein. The system memory 56a can include volatile memory, such as, for example, RAM (random-access memory). The storage memory 56b can be non-volatile or persistent memory such as, for example, ROM (read-only memory), flash memory, ferroelectric RAM, most types of magnetic computer storage devices (e.g. hard disk drives, solid state drives, floppy disks, and magnetic tape), or optical discs. The computer processing device 50 includes one or more associated displays 58 for indicating the autonomic engagement response to the stimulus. The system memory 56a and/or storage memory 56b may store instructions that are executable by the processor 54 to perform the functionalities described herein. The display 56 can be a touch-sensitive display, which can provide touch control buttons and keys.

As shown, the processing hardware 52 and the display 58 communicate with one another over a communication bus or network 60. Additionally or alternatively, the computer processing device 50 can include one or more peripheral input and output ports for connection and use with other peripheral input, output, or storage devices. The components of the computer processing device 50 can be integrated with one another or be separately housed components. For example, the processing hardware 52 can be housed separately from the display 58. Alternatively, the display 58 can be housed with the processing hardware 52 in a single assembly. In some embodiments, the computer processing device 50 can be embodied using a general purpose programmable computer. A general purpose programmable computer can be a personal computer, laptop computer, Ultrabook computer, netbook computer, handheld computer, tablet computer, smart phone, or other form of computational device with an appropriate operating system. In other embodiments, the computer processing device 50 can be a specialized computer specifically designed and programmed to function with the neurostimulator 22 described herein.

Figure 4B:
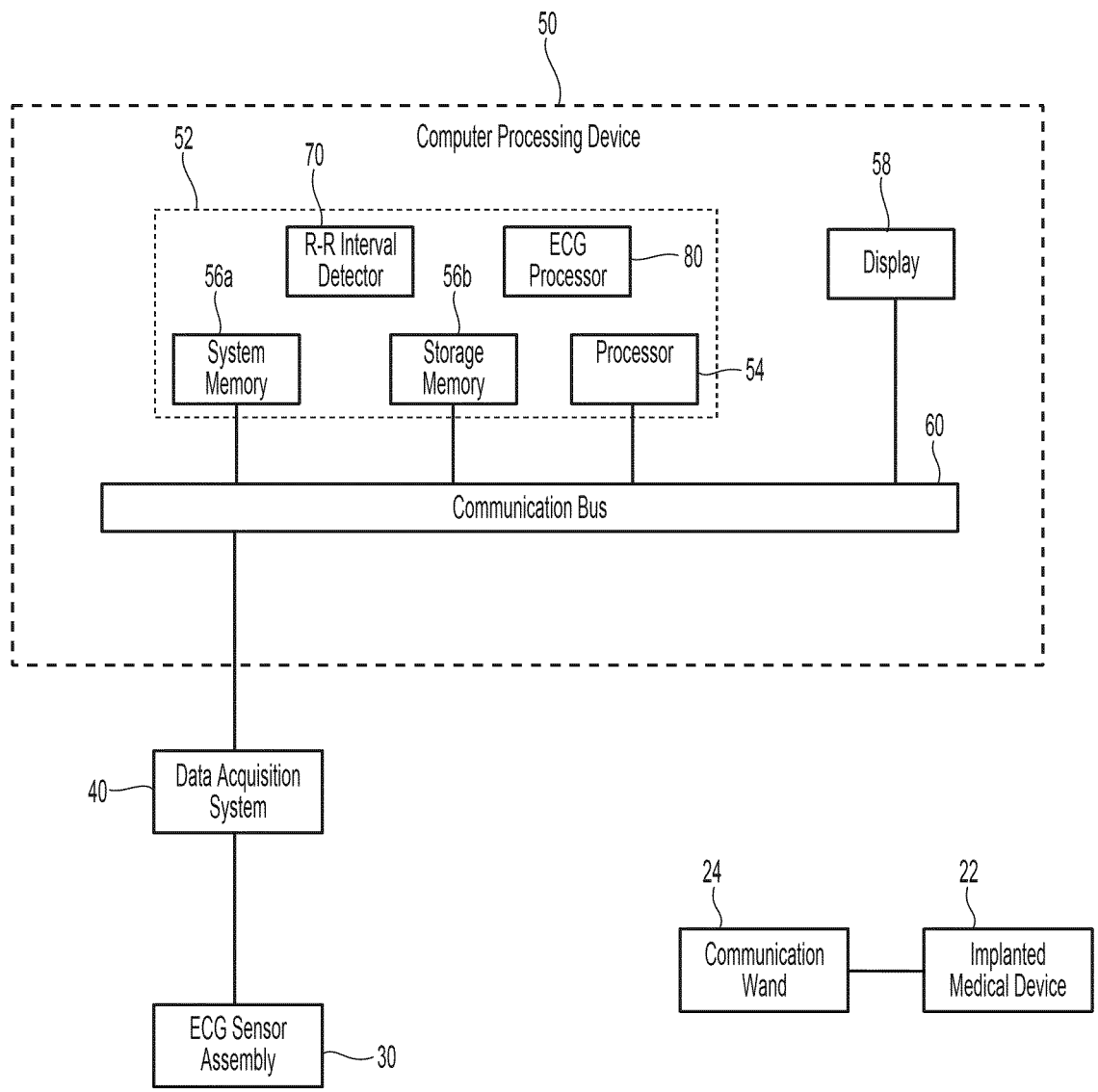
FIG. 4B is another schematic view of components of the system of FIG. 2A, shown without the transmission detection cable, according to an exemplary embodiment.

Referring back to FIGS. 2A and 2B, in the system 10, the computer processing device 50 is coupled to either the first and second interface communication assemblies 20, 30 (as shown in FIG. 2A) or only the second interface assembly 30 (as shown in FIG. 2B) by a data acquisition system 40. The data acquisition system 40 provides for digital conversion of incoming signals coming from the ECG sensor assembly 30 or both of the interface communication assemblies 20, 30 (e.g., the wand assembly 20 and the ECG sensor assembly 30). The data acquisition system 40, the processing hardware 52, and the display 58 communicate with one another over a communication bus or network 60 (e.g., as shown in FIGS. 4A and 4B). In some embodiments, the data acquisition system 40 for use in the system 10 is the BIOPAC MP36R from BIOPAC® Systems, Inc., which can simultaneously capture signals from multiple devices or sources. Additionally, in some embodiments, the computer processing device and the data acquisition system are different systems (e.g., shown as computer processing device 50 and data acquisition system 40 in FIGS. 2A and 2B), while in other embodiments, the computer processing device and data acquisition system are incorporated into a single system (e.g., shown as computer processing device 50' in FIGS. 2A and 2B).

In some embodiments, the communication assembly 20 wirelessly communicates with the neurostimulator 22 by providing control signals or commands to define parameters of the stimulation signal or pulses to be delivered by the neurostimulator 22 to the vagus nerve. In some embodiments, as shown in FIG. 2A, the communication assembly 20 includes an external programming wand 24 and a wand transmission detection cable 26. The programming wand 24 wirelessly communicates with the implanted device 22 by telemetry or radio frequency signal. Embodiments of the external programming wand 24 are described, for example, in U.S. Pat. Nos. 9,770,599 and 9,950,169. A commercially available embodiment of the wand 24 includes NeuroCybernetic Prosthesis (NCP®) Programming Wand Model 201. The wand 24 is a hand-held device that can transmit programming and interrogation information signals or commands to the implantable neurostimulator 22, such as, for example, the VITARIA™ Model 7103 Pulse Generator. The programming wand 24 alone or in conjunction with a computer and appropriate firmware, such as, for example VNS Therapy Programming Software, can store and retrieve telemetry data and revise stimulus signal parameters from the pulse generator 22.

The wand transmission detection cable 26 is associated with the external programmer or wand 24 to detect or determine the stimulation delivery from the neurostimulator 22 to the vagus nerve 15 of the subject patient SP. In some embodiments, the wand transmission detection cable 26 may be used to detect the telemetry signals transmitted between the external wand 24 and the neurostimulator 22, and transmit the telemetry signals back to the data acquisition system 40 and computer processing device 50 to be used to determine the stimulation delivery schedule of the neurostimulator 22 to the vagus nerve 15. For example, the stimulation delivery from the neurostimulator 22 may have a duty cycle with a stimulation ON period and a stimulation OFF period, and determining the stimulation delivery schedule may include determining a timing of the stimulation ON period and the stimulation OFF period of the stimulation of the neurostimulator 22.

Alternatively, as mentioned above, in some embodiments, the wand transmission detection cable 26 may be omitted (as shown in FIG. 2B). In these embodiments, the external wand 24 may still be used to provide control signals or commands to define parameters of the stimulation signal or pulses to be delivered by the neurostimulator 22 to the vagus nerve, as described above, but the computer processing device 50 may not receive any signals from the external wand 24 via the wand transmission detection cable 26. Instead, the computer processing device 50 may be configured to inferentially or implicitly determine or derive the stimulation delivery schedule from the neurostimulator 22 to the vagus nerve 15 based on the ECG-suitable signal captured by the ECG sensor assembly 30. For example, the computer processing device 50 may utilize one or more known stimulation parameters of the neurostimulator 22 in conjunction with the ECG-suitable signal (e.g., the periodic waveform with repeating "cardiac cycles," shown in FIGS. 13, 14, and 18) captured by the ECG sensor assembly 30 to detect or identify the stimulation ON period and the stimulation OFF period of the duty cycle of the stimulation signal within the ECG-suitable signal to determine the stimulation delivery schedule of the neurostimulator 22, as will be discussed further below, with reference to FIGS. 7 and 8. As such, in some instances, the neurostimulator 22 and/or the external wand 24 may be part of a separate system provided by a different entity than the computer processing device 50 and the ECG sensor assembly 30. However, in some other instances, the neurostimulator 22, the external wand 24, the ECG sensor assembly 30, and the computer processing device 50 may all be part of a single system provided by a single entity.

By determining the stimulation delivery schedule of the neurostimulator 22 (e.g., either directly via the telemetry signals captured by the detection cable 26 or inferentially via the ECG-suitable signal captured by the ECG sensor assembly 30), the capture or recording of the subject's ECG-suitable signal can be synchronized with the ON period and OFF period of the stimulation signal based on the determined stimulation delivery schedule to effectively analyze various stimulation response characteristics associated with the neurostimulation signal provided to the patient.

In some implementations, the second interface assembly 30 is embodied as an ECG cable assembly with three leads or clips 32a, 32b, 32c for respectively connecting to three electrodes or contacts, for example, placed on the wrists of the subject patient SP. As seen in FIG. 2A, two leads 32a, 32b are connected to two electrodes on the left wrist and the remaining lead 32c is connected to a single electrode on the patient's right wrist. In other implementations, the second interface assembly 30 may be embodied with fewer or more leads or clips and/or the leads may be placed different, as appropriate for a given application.

The computer processing device 50 operates under the control of one or more software applications, which are executed as program code as a series of process or method modules or steps by the programmed computer hardware. In some embodiments, a computer readable medium, such as a non-transitory computer readable medium, of the processing hardware 52 stores a program that can cause the computer processing device 50 to execute one or more processes described herein for assessing vagus nerve stimulation treatment.

In some embodiments, the system 10 processes the ECG-suitable signal response to determine the ECG waveform and the R-R intervals to derive heart rate dynamics in assessment of the stimulus treatment. Moreover, the system 10 distinguishes or identifies which portions of the ECG signal or waveform response correspond to the delivery of stimulation signal, i.e., the ON periods of the periodic stimulation signal, and which portions of the ECG signal or waveform response correspond to the rest period, i.e., over the OFF periods, of the periodic stimulation signal. By segregating ECG signals or portions of the ECG waveforms and their derivative components by ON period and OFF period, the ECG signals/waveforms and the heart rate dynamics derived therefrom can be compared to assess the extent of autonomic engagement resulting in the delivered stimulation signal.

Referring again to FIG. 4A, the computer processing device 50 and its hardware includes and executes firmware programming that provides for an R-R interval detector 70 and an ECG processor 80 for carrying out the assessment methods described herein. The R-R interval detector 70 and ECG processor 80 and the associated methods described herein can be implemented using appropriate software programming for signal processing and hardware configuration. For example, an appropriate "graphical program" can be used to represent data structures and/or program instructions in memory (e.g., the system memory 56a and/or storage memory 56b) of the computer processing device 50 to carry out the signal processing, instrument access, and assessment methods described herein. An exemplary graphical program development environment in which to create a program for use in the system 10 includes LabVIEW from National Instruments Corp.

Figure 5:
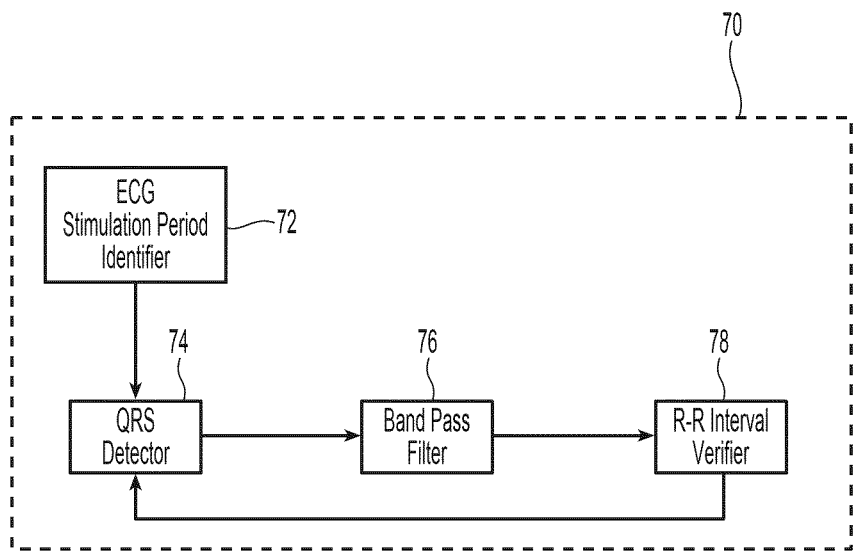
FIG. 5 is a schematic view of an embodiment of an R-R interval detector for use in the system of FIG. 2A, according to an exemplary embodiment.
Figure 6:
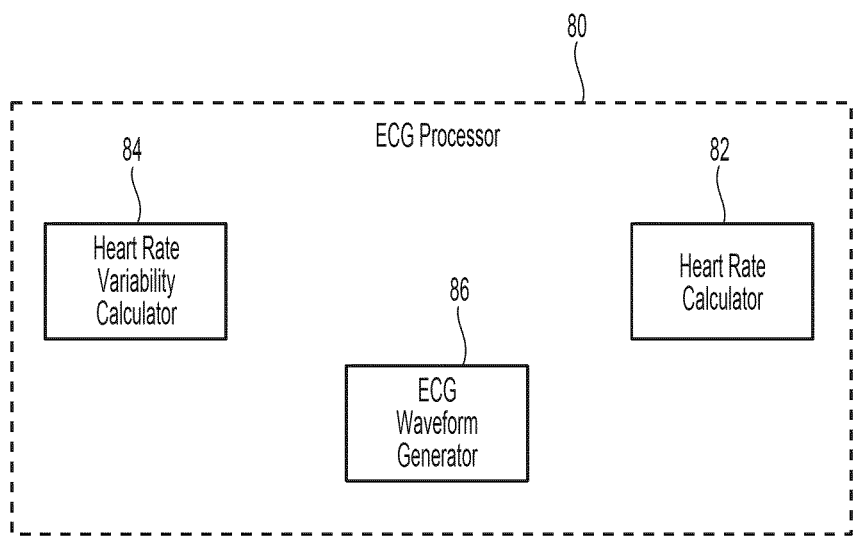
FIG. 6 is a schematic view of an embodiment of an ECG processor for use in the system of FIG. 2A, according to an exemplary embodiment.

Embodiments of the R-R interval detector 70 and the ECG processor 80 are shown in FIGS. 5 and 6, respectively. The R-R interval detector 70 of FIG. 5 includes an ECG stimulation period identifier 72, a real-time QRS detector 74, a band pass filter 76, and an R-R interval verifier 78. The ECG stimulation period identifier 72 identifies portions of the incoming ECG response as corresponding to either the ON period or the OFF period of the stimulation signal. The real-time QRS detector 74 is configured to identify the QRS-wave or complex within the ECG-suitable signal. The band pass filter 76 is configured to identify the R-wave by detecting a maximum amplitude of the ECG-suitable signal corresponding to the R-wave.

Figure 18:
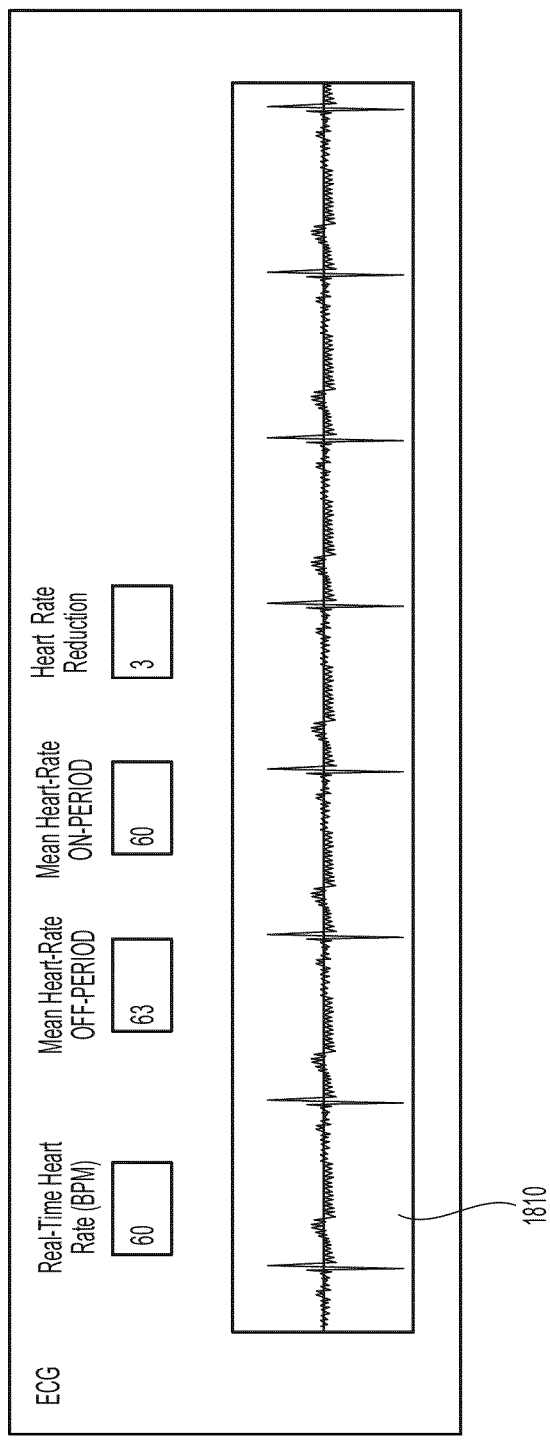
FIG. 18 is an illustrative view of a digital replica of an ECG waveform response and various heart rate dynamics generated from the method of FIG. 6, according to an exemplary embodiment.

As shown in FIG. 6, the ECG processor 80 includes a heart rate calculator 82, a heart rate variability calculator 84, and an ECG waveform generator 86. The heart rate calculator 82 is configured to determine, in real-time, the mean heart rate for each ON period of stimulation signal delivery and each OFF period of rest in a given treatment cycle. The heart rate variability calculator 84 is configured to determine heart rate variability for assessing response to the vagus nerve stimulation. In particular, the variability calculator 84 may determine a difference in the heart rate variability response between the ON period and the OFF period of stimulation. The ECG waveform generator 86 is configured to generate and display a digital replica of the ECG waveform on the display 58 (as shown in FIG. 18).

Figure 7:
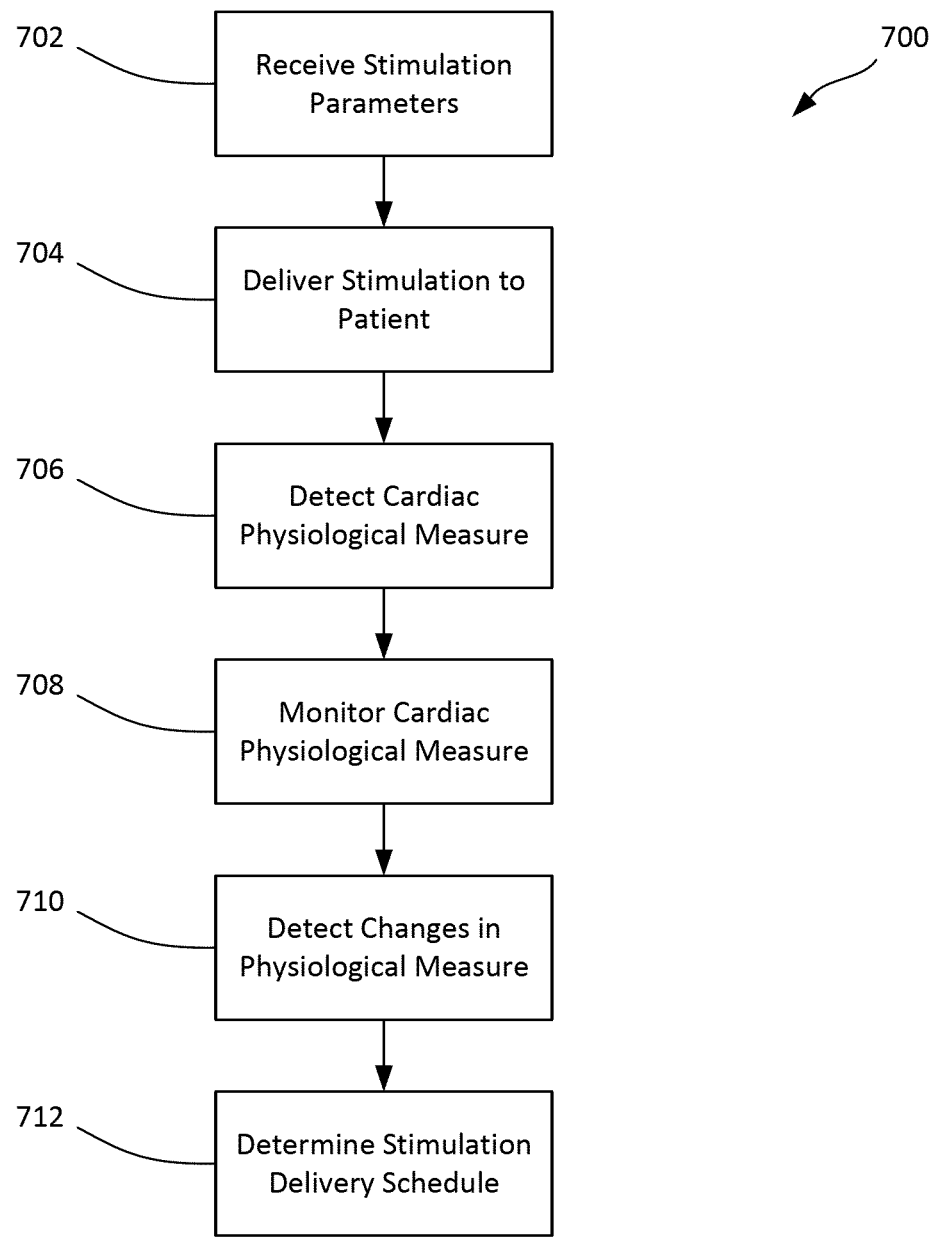
FIG. 7 is a flowchart of a method for determining a stimulation delivery schedule, according to an exemplary embodiment.

Referring now to FIG. 7, a method 700 of inferentially determining a stimulation delivery schedule of the neurostimulator 22 is shown, according to an exemplary embodiment. In some instances, the method 700 may be performed by the computer processing device 50 described above. The method 700 may begin at step 702 with the computer processing device 50 receiving known stimulation parameters of the stimulation to be provided by the neurostimulator 22. For example, in some instances, a user may input the known stimulation parameters of the neurostimulator 22 into the computer processing device 50 via the touchscreen display 56, a keyboard, or any other suitable input device. In some instances, the user may provide stimulation timing parameters, such as a stimulation ON period duration, a stimulation OFF period duration, and/or an overall stimulation cycle duration (i.e., including both the stimulation ON period and the stimulation OFF period). Specifically, in some instances, the user may provide both the stimulation ON period duration and the stimulation OFF period duration. In some other instances, the user may provide only the overall stimulation cycle duration. In some instances, the user may additionally provide various stimulation intensity parameters, such as, for example, output current, pulse width, signal frequency, and duty cycle.

In some instances, once the user has input the one or more known stimulation parameters of the neurostimulator 22 into the computer processing device 50, stimulation may then be delivered by the neurostimulator 22 to the patient, at step 704. However, in some instances, the stimulation may be initiated before, during, or after the user has provided the known stimulation parameters to the computer processing device 50.

While the stimulation is being provided to the patient by the neurostimulator 22, one or more cardiac physiological measures of the patient may be detected, at step 706. For example, the one or more cardiac physiological measures may be detected by the computer processing device 50 via the ECG-suitable signal received from the ECG sensor assembly 30. The one or more cardiac physiological measures may include various heart rate dynamics of the patient. For example, the heart rate dynamics of the patient may include a heart rate, a heart rate variability, an R-R interval, a P-P interval, a T-T interval, a P-R interval, a Q-T interval, a heart rate variability, and/or any other suitable heart rate dynamic of the patient.

Once the one or more cardiac physiological measures have been detected, the computer processing device 50 may monitor the one or more cardiac physiological measures while the stimulation is provided to the patient by the neurostimulator 22, at step 708. While monitoring the one or more cardiac physiological measures, the computer processing device 50 may then detect various changes in the one or more cardiac physiological measures within the monitored ECG data, at step 710.

For example, the computer processing device 50 may detect a first change (e.g., an increase or a decrease) in the one or more cardiac physiological measures at a first time within the monitored ECG data. The first time of the first detected change may be identified as a first transition time in the duty cycle where the neurostimulation signal provided by the neurostimulator 22 transitions between the stimulation OFF period and the stimulation ON period.

The computer processing device 50 may then detect a second change in the one or more cardiac physiological measures. For example, in some instances, the one or more cardiac physiological measures may return (i.e., increase or decrease) back to its original value at a second time, after the first time, within the monitored ECG data. The second time of the second detected change in the one or more cardiac physiological measures may similarly be identified as a second transition time in the duty cycle where the neurostimulation provided by the neurostimulator 22 transitions between the stimulation OFF period and the stimulation ON period.

After detecting the changes in the one or more cardiac physiological measures, the computer processing device 50 may then determine a stimulation delivery schedule of the neurostimulation provided by the neurostimulator 22, at step 712. The stimulation delivery schedule may be an identification of the timing of the stimulation ON periods and the stimulation OFF periods of the stimulation signal.

Figure 8:
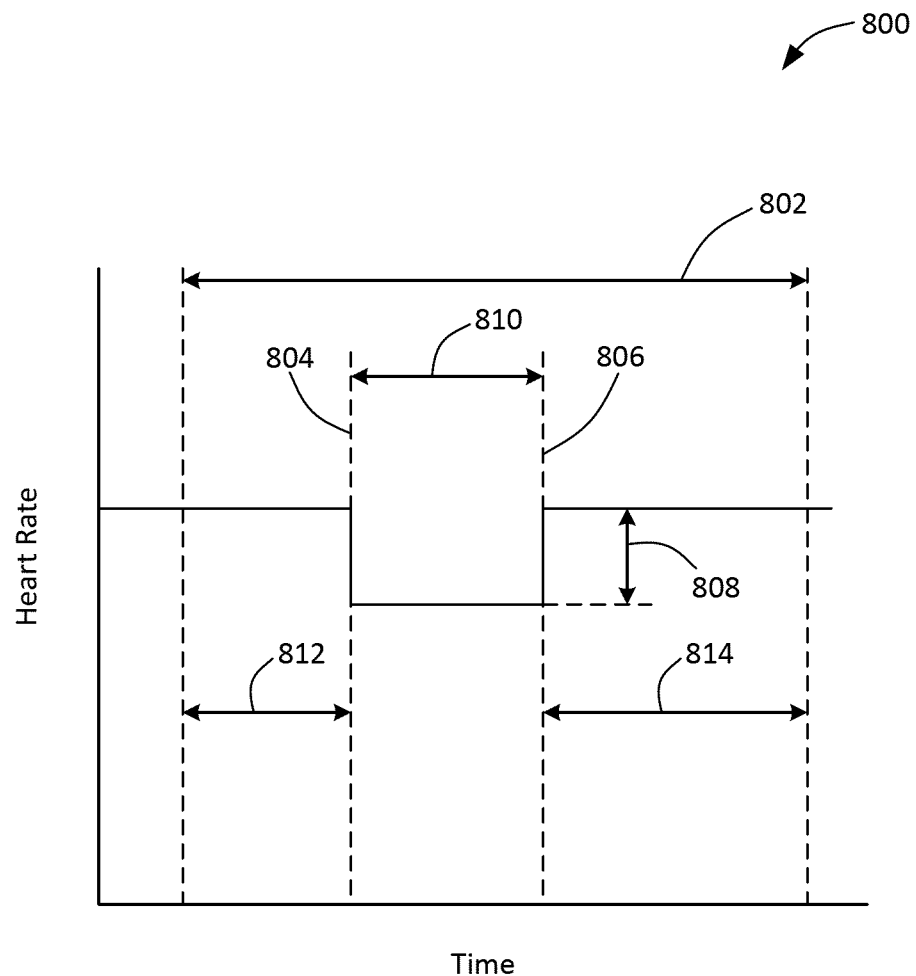
FIG. 8 is an illustrative graphic of a heart rate response as a function of time during vagus nerve stimulation therapy using the system of FIG. 2A, according to an exemplary embodiment.

Referring now to FIG. 8, to determine the stimulation delivery schedule, the computer processing device 50 may split the monitored ECG data into a plurality of consecutive time periods ("stimulation cycle periods"), each equal in duration to a single overall stimulation cycle (stimulation cycle period duration 802). The computer processing device 50 may then average the plurality of stimulation cycle periods within the monitored ECG data to generate an averaged stimulation cycle period 800 having an averaged first transition time 804, an averaged second transition time 806, and an averaged detected change 808 in the one or more cardiac physiological measures.

In some instances, the computer processing device 50 may use the stimulation timing parameters to identify the stimulation ON period and the stimulation OFF period within the averaged stimulation cycle period 800. For example, if the user provided the stimulation ON period duration and the stimulation OFF period duration, the computer processing device 50 may compare a time period 810 between the averaged first transition time 804 and the averaged second transition time 806 to the stimulation ON period duration and the stimulation OFF period duration. Based on this comparison, the computer processing device 50 may determine that the time period 810 corresponds to one of the stimulation ON period or the stimulation OFF period, and thus identify when the stimulation ON period and the stimulation OFF period are occurring within the averaged stimulation cycle period 800.

For example, if the time period 810 corresponds to the stimulation ON period duration, the computer processing device 50 may determine that the stimulation ON period is occurring between the averaged first transition time 804 and the averaged second transition time 806 (i.e., stimulation is being applied by the neurostimulator 22 during the time period 810 between the averaged first transition time 804 and the averaged second transition time 806). Accordingly, the computer processing device 50 may further determine that the stimulation OFF period is occurring during both a time period 812 before the averaged first transition time 804 and a time period 814 after the averaged second transition time 806 (i.e., stimulation is not being applied by the neurostimulator 22 during the time period 812 before the averaged first transition time 804 and during the time period 814 after the averaged second transition time 806).

Alternatively, if the user did not provide either the stimulation ON period duration or the stimulation OFF period duration, the computer processing device 50 may instead use the overall stimulation cycle duration (e.g., the stimulation cycle period duration 802) and the stimulation intensity parameters to be delivered by the neurostimulator 22 to identify the stimulation ON period and the stimulation OFF period within the averaged stimulation cycle period 800. For example, based on the stimulation intensity parameters, the computer processing device 50 may determine an expected change in the one or more cardiac physiological measures based on an expected cardiac response of the patient to the neurostimulation. This expected cardiac response may be based upon historical stimulation data provided to and stored on the computer processing device 50. For example, as depicted in FIG. 1, a decrease in heart rate may be expected during the stimulation ON period at higher stimulation intensities and an increase in heart rate may be expected during the stimulation ON period at lower stimulation intensities. It will be appreciated that various other cardiac responses may be expected for a variety of other monitored cardiac physiological measures. These expected changes may include expected increases or decreases in the monitored cardiac physiological measure at either high or low intensities, as appropriate for a given cardiac physiological measure.

With reference again to FIG. 8, the computer processing device 50 may compare the expected change in the one or more cardiac physiological measures to the averaged detected change 808 in the one or more cardiac physiological measures at either the averaged first transition time 804 or the averaged second transition time 806 to identify the stimulation ON period and the stimulation OFF period within the averaged stimulation cycle period 800. For example, if the stimulation intensity is sufficiently high (based on the historical stimulation data) and the averaged detected change 808 at the averaged first transition time 804 is a decrease in the heart rate (or a corresponding expected change in any other monitored cardiac physiological measure), the computer processing device 50 may determine that stimulation is being applied by the neurostimulator 22 during the time period 810 between the averaged first transition time 804 and the averaged second transition time 806 (i.e., the stimulation ON period is occurring between the averaged first transition time 804 and the averaged second transition time 806). Similarly, the computer processing device 50 may further determine that stimulation is not being applied by the neurostimulator 22 during the time period 812 before the averaged first transition time 804 and during the time period 814 after the averaged second transition time 806 (i.e., the stimulation OFF period is occurring during the time period 812 before the averaged first transition time 804 and during the time period 814 after the averaged second transition time 806).

Once the computer processing device 50 has identified the stimulation ON period and the stimulation OFF period within the averaged stimulation cycle period 800, the computer processing device 50 may then apply this information to each stimulation cycle period within the previously-monitored ECG data, as well as to each subsequently monitored stimulation cycle period, to identify each of the stimulation ON periods and stimulation OFF periods in real-time within the monitored ECG data, thus effectively determining the stimulation delivery schedule of the neurostimulator 22.

As discussed in greater detail below, with reference to FIGS. 9, 10, and 15, by determining the stimulation delivery schedule of the neurostimulator 22, the monitored ECG data may be synchronized with the stimulation ON periods and the stimulation OFF periods. This synchronized ECG data may be used by physicians to analyze various aspects of the neurostimulation treatment provided to the patient. Accordingly, the synchronized ECG data allows for physicians to effectively monitor the patient and manipulate the stimulation intensity parameters to ensure that the neurostimulation provided to the patient elicits a cardiac response within the neural fulcrum zone, thereby improving the efficacy of the neurostimulation therapy.

Further, because the method 700 allows for the inferential determination of the stimulation delivery schedule of the neurostimulator 22, the transmission detection cable 26 may be completely omitted from the system 10 (as shown in FIGS. 2B and 4B). This omission of the transmission detection cable 26 may be beneficial for a variety of reasons. For example, the wand detection cable 26 is traditionally expensive to manufacture and prone to breaking. Additionally, the wand detection cable 26 must be properly placed on the external wand 24 to function as intended (e.g., effectively detect the telemetry signals of the external wand 24). Further, the wand detection cable 26 generally requires the user to perform a programming event on the neurostimulator 22 in order to synchronize the monitored ECG data with the neurostimulation, even in the case that the stimulation parameters will be unchanged. Accordingly, by allowing for the omission of the transmission detection cable 26, the method 700 performed by the computer processing device 50 effectively reduces the overall cost of the system 10, eliminates the need for proper placement of the wand detection cable 26 on the external wand 24, and allows for the synchronization of the monitored ECG data with the neurostimulation provided by the neurostimulator 22 without the need to perform a programming event.

Figure 9:
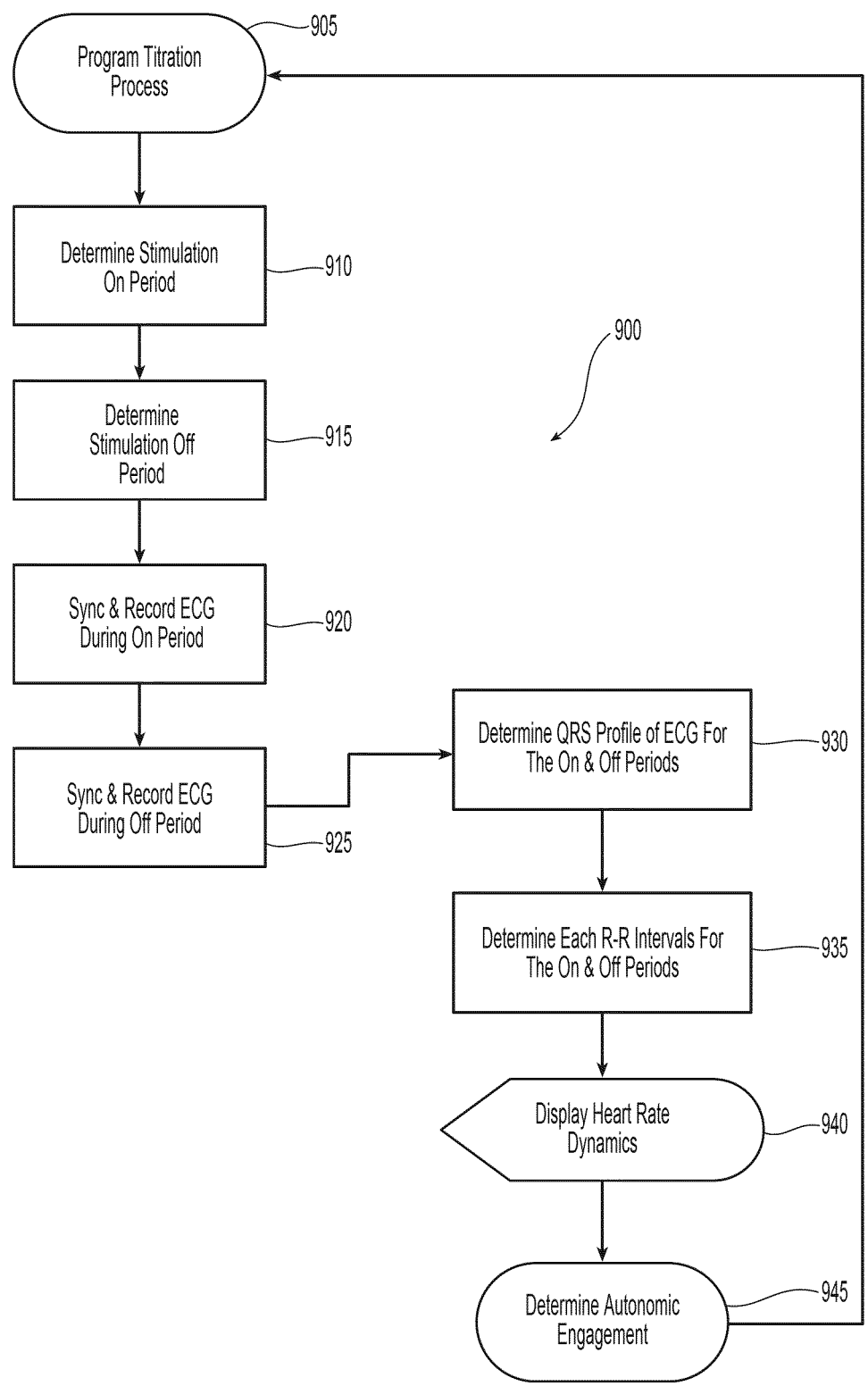
FIG. 9 is a flow chart of a method for assessing autonomic engagement response to vagus nerve stimulation therapy using the system of FIG. 2A, according to an exemplary embodiment.

Shown in FIG. 9 is a process 900 for capturing and analyzing the ECG-suitable signal response during vagus nerve stimulation treatment, according to an exemplary embodiment. At an initial step 905, the titration or stimulation delivery process of the neurostimulator 22 is programmed (e.g., utilizing the external wand 24). In some instances, programming the titration or stimulation delivery process may include setting an initial set of stimulation intensity parameters, a titration rate for one or more of the stimulation intensity parameters, and a set of one or more target stimulation intensity parameters.

Once the titration or stimulation delivery process has been programmed, the computer processing device 50 may then determine a stimulation delivery schedule of the stimulation signal to be delivered from the neurostimulator 22 to the vagus nerve. As discussed herein, the stimulation signal may be periodic having stimulation ON periods in which stimulation of a particular current amplitude and frequency is delivered and stimulation OFF periods of rest in which no stimulation signal is delivered to the vagus nerve. In some instances, determining the stimulation delivery schedule includes identifying or determining the stimulation ON periods (step 910) and determining or identifying the stimulation OFF periods (step 915) of the stimulation signal within the ECG-suitable signal.

For example, in some instances, the stimulation ON periods and the stimulation OFF periods of the stimulation signal may be identified directly utilizing the first interface 20. That is, the programming wand 24 may be placed in communication with the neurostimulator 22, and the wand transmission detection cable 26 in combination with the computer processing device 50 may detect the inductive telemetry signal between the components. The computer processing device 50 may then process the inductive telemetry signals to determine the stimulation ON periods and determine the stimulation OFF periods of the stimulation signal within the ECG-suitable signal. Alternatively, in the case that the transmission detection cable 26 is omitted (as shown in FIGS. 2B and 4B), the computer processing device 50 may inferentially determine the stimulation ON periods and the stimulation OFF periods of the stimulation signal within the ECG-suitable signal, as discussed above, with reference to FIGS. 7 and 8.

With the stimulation delivery schedule determined, the computer processing device 50 may then perform synchronization and recordation steps 920, 925 in which an ECG-suitable signal is captured and recorded over each of the stimulation ON periods and the stimulation OFF periods. Although FIG. 9 shows the determination and recordation steps as discrete steps, the steps may be carried out sequentially, concurrently, or in an alternate order.

Having captured and identified the ECG-suitable signals corresponding to each of the stimulation ON period and stimulation OFF period in the stimulation signal, the computer processing device 50 may then determine the QRS complex profile in the corresponding ECG waveforms for each period of the stimulation signal, at step 930. The computer processing device 50 may then determine each R-R interval between consecutive QRS complexes in each ECG-suitable signal corresponding to the stimulation ON periods and the stimulation OFF periods within the stimulation signal. Accordingly, various heart rate dynamic response characteristics, such as, for example, instantaneous heart rate, mean heart rate, and heart rate variability, can be determined and displayed, at step 940, for each of the ON period and OFF period in the stimulation signal. The process 900 may then conclude with an assessment step 945 in which the autonomic engagement response can be determined, indicated, and displayed for the subject patient and/or clinician.

Based on the determined autonomic engagement response, the clinician may then decide to make one or more modifications to the titration process of the neurostimulator 22 to achieve a higher level of autonomic engagement. Accordingly, the clinician continue to repeat the process 900, making iterative modifications to the titration process, until a stimulation signal that elicits a cardiac response within the neural fulcrum zone is achieved.

Figure 10:
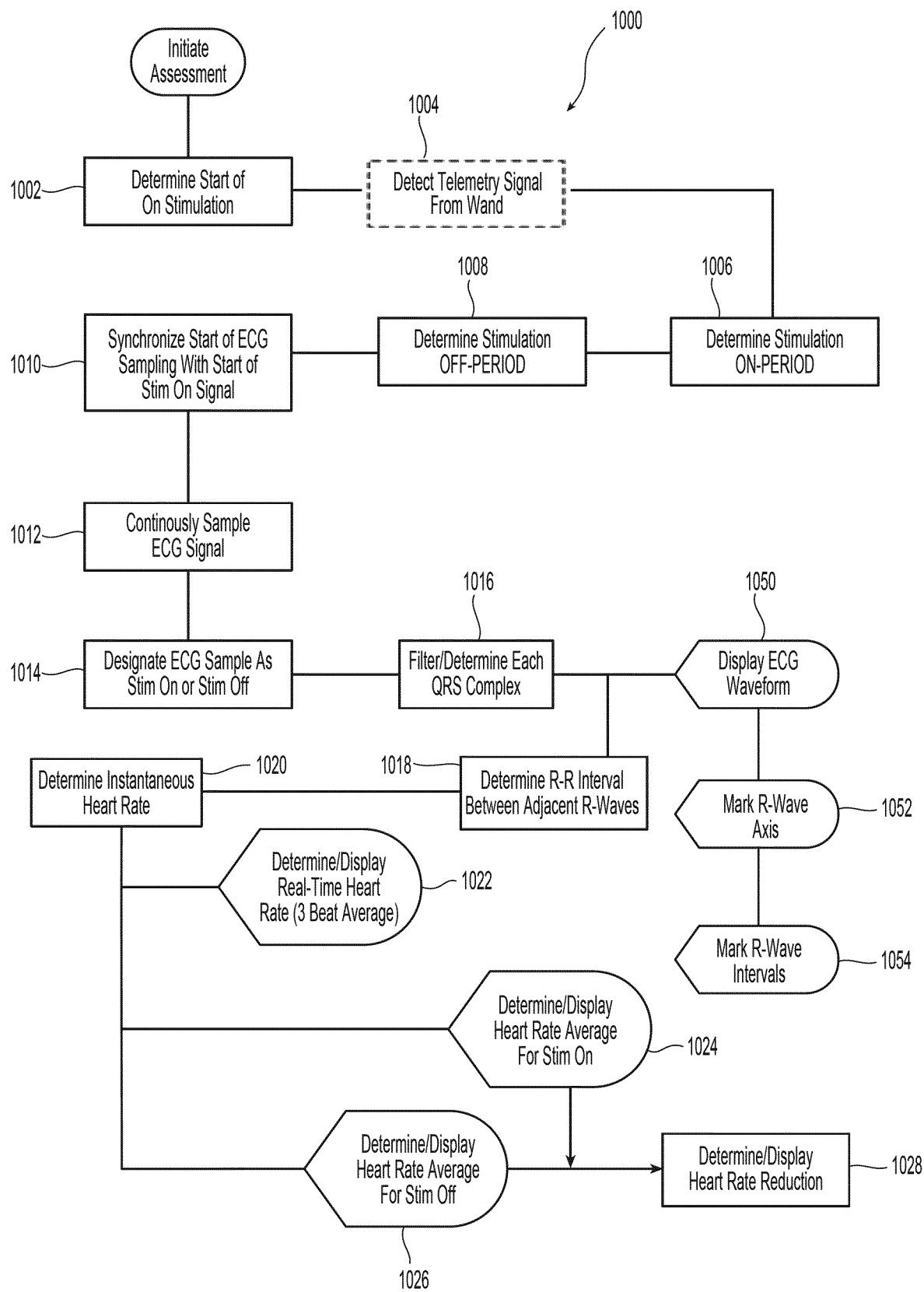
FIG. 10 is another embodiment of a method for assessing autonomic engagement response to vagus nerve stimulation therapy using the system of FIG. 2A, according to an exemplary embodiment.

Shown in FIG. 10 is an embodiment of an assessment process 1000. With the subject patient SP connected to the system 10, as shown in FIG. 2A, and the implanted neurostimulator medical device 22 delivering a stimulation signal to the vagus nerve of the patient, the process of assessment 1000 begins with a determination step 1002 to determine the start of stimulation delivery for synchronizing recordation of the cardiac response.

In some embodiments, the wand transmission detection cable 26 may optionally be used to detect the inductive telemetry signal between the external wand 24 and the neurostimulator 22, at step 1004. In these instances, the computer processing device 50 may process the inductive telemetry signals to determine the stimulation ON periods (step 1006) and determine the stimulation OFF periods (step 1008) of the stimulation signal. Alternatively, step 1004 may be omitted from the process 1000, and the computer processing device 50 may inferentially determine the stimulation ON periods (step 1006) and the stimulation OFF periods (step 1008) of the stimulation signal, as discussed above, with reference to FIGS. 7 and 8. With the stimulation ON periods and the stimulation OFF periods of the stimulation signal determined, the computer processing device 50 may then synchronize the sampling of the ECG-suitable signal with the start of the stimulation ON period of the delivered stimulation signal, at step 1010.

Figure 11:
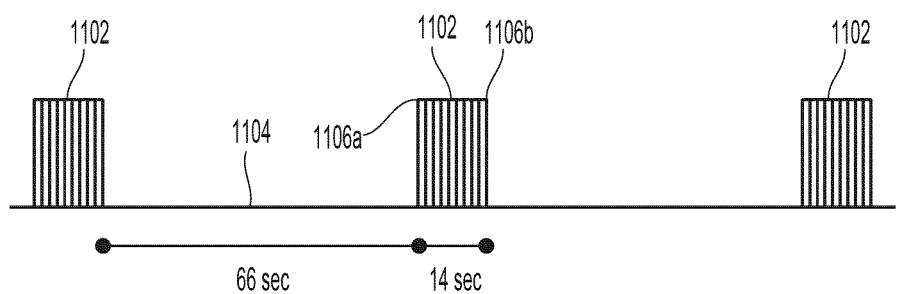
FIG. 11 is an illustrative schematic view of a stimulus signal, according to an exemplary embodiment.

Shown in FIG. 11 is an exemplary vagus stimulation signal 1100 defined by one or more of the following parameters: output current amplitude or intensity, signal frequency, or pulse width. The vagus stimulation signal 1100 is delivered in a cyclical manner in which each cycle of is defined by a stimulation ON period 1102 in which the stimulation signal is delivered to the vagus nerve and an OFF period or rest period 1104 in which no stimulation is delivered. The stimulation ON period 1102 occurs at a constant interval with the OFF periods 1104 of rest between the repeating stimulation ON periods 1102. In some embodiments, a treatment cycle can be defined by a combination of on and off times selected from the following exemplary stimulation ON periods: 7 sec, 14 sec, 21 sec, 30 sec, 50 sec, and 60 sec; and exemplary OFF periods: 12 sec, 18 sec, 24 sec, 30 sec, 42 sec, 54 sec, 66 sec, 78 sec, 90 sec, 120 sec, 180 sec, and 300 sec. For example, one exemplary treatment cycle is defined by a 14 second "ON period" and a 66 second "OFF period" (as shown in FIG. 11).

Figure 12:
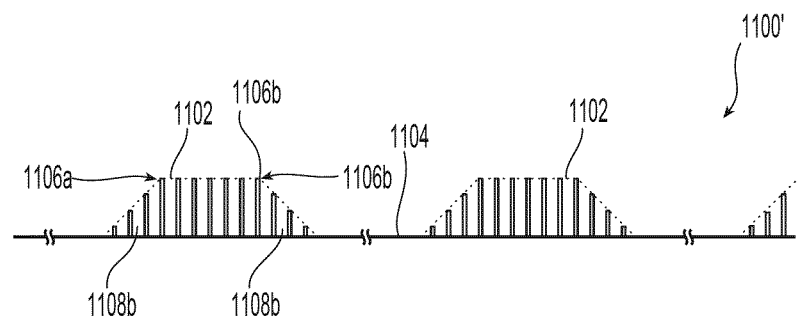
FIG. 12 is an illustrative schematic view of another stimulus signal, according to an exemplary embodiment.

As discussed above, a cycle of stimulation delivery is defined by a consecutive ON period and OFF period. In some embodiments of treatment, there are 5-10 cycles. Each ON period is defined by repeating pulse signals at a defined output current amplitude or intensity, signal frequency, and pulse width. In one exemplary ON period, the pulse signals are defined by an output current of up to 3.0 mA, a frequency of 5-10 Hz, and a pulse width at 250-300 micro-seconds ("μsec"). Accordingly, each ON period is defined by an initiating pulse 1106a and a terminating pulse 1106b that are spaced apart over a time duration defining the ON period 1102. The OFF period 1104 is thus defined by the time duration between a terminating pulse 1106b of one ON period 1102 and the initiating pulse 1106a of the consecutive, subsequent ON period 1102. Shown in FIG. 12 is another embodiment of a stimulation signal 1100', which includes a ramp up period 1108a to the initiating pulse 1106a and a ramp down period 1108b from the terminating pulse 1106b (e.g., with the ramping up period 1108a and the ramping down period 1108b both being at a constant rate).

Figure 13:
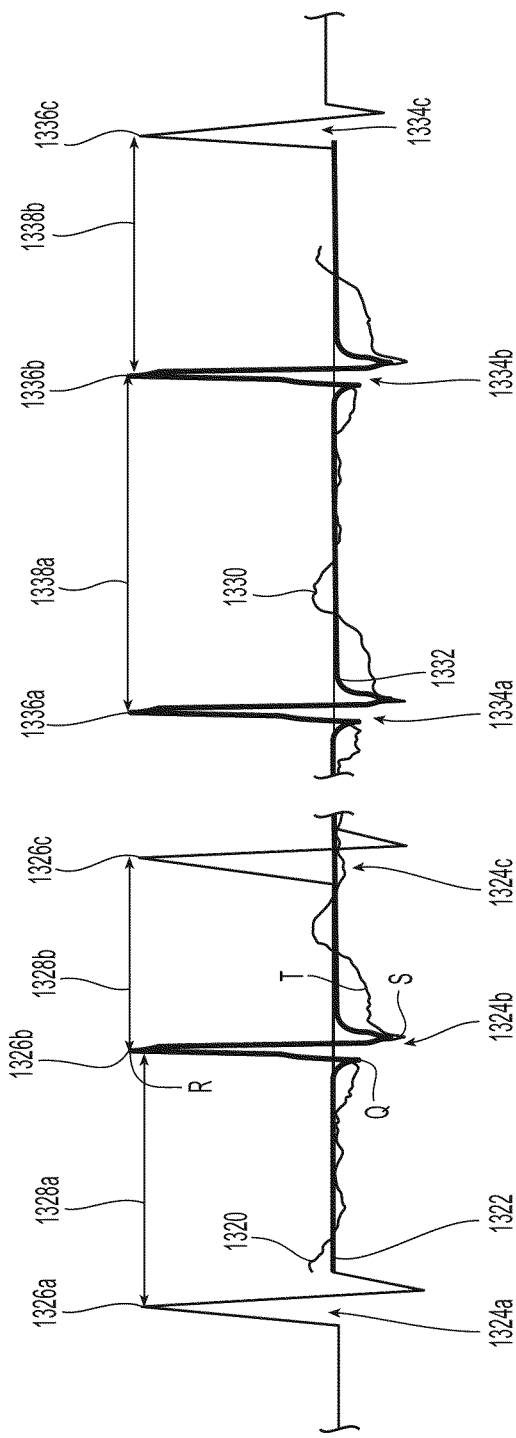
FIG. 13 is an illustrative view of an ECG waveform response in a subject patient to a vagus nerve stimulation treatment, according to an exemplary embodiment.

Referring again to FIG. 10, with the start of the ECG signal recording synchronized with the stimulation signal, the ECG-suitable signal is continuously sampled at step 1012 by the data acquisition system 40 and the computer processing device 50. For example, the ECG-suitable signal is sampled at a rate of 200 samples per second at a rate suitable for analysis and processing as described herein. In some embodiments, the ECG-suitable signal is recorded for at least one successive pair of ON and OFF periods. More particularly, in some embodiments, the ECG-suitable signal is recorded over a plurality of successive pairs of ON and OFF periods. In an exemplary ECG processing step 1014, the digitally converted ECG-suitable signal is segregated and designated into portions that correspond to the ECG response to the ON period of stimulation delivery and the ECG response to the resting OFF period. For example, illustrated in FIG. 13 is a first portion 1320 of the sampled ECG-suitable signal corresponding to the ON period of the stimulation signal and a second portion 1330 of the sampled ECG-suitable signal corresponding to the OFF period of the stimulation signal.

With the ECG-suitable signal segregated and designated appropriately, the R-R interval detector 70 may filter and/or determine each QRS complex within the ECG-suitable signal at step 1016. For example, each of the designated portions of the ECG waveform response (e.g., the first portion 1320 corresponding to the ON period and the second portion 1330 corresponding to the OFF period) of the stimulation signal is processed to determine the components of the ECG waveform for further analysis and digital reconstruction. In some embodiments, the real-time QRS detector 74 of the R-R interval detector 70 identifies the QRS-wave or complex and the band pass filter 76 identifies the R-wave by detecting a maximum amplitude corresponding to the R-wave. For example, as indicated in FIG. 13, QRS complexes 1324a, 1324b, 1324c for the ON period ECG waveform portion 1320 and QRS complexes 1334a, 1334b, 1334c of the OFF period ECG waveform portion 1330 are identified within the ECG waveform. Further, each of the R-waves (1326a, 1326b, 1326c) (1336a, 1336b, 1336c) of the QRS complexes may also be initially identified from baselines 1322, 1332.

The R-R interval (1328a, 1328b for the ON period) (1338a, 1338b for the OFF period), or time period between adjacent R-waves in the ECG waveform or equivalent ECG characterization, is then determined, at step 1018, and verified by the R-R interval verifier 78 in real-time. The R-R interval verifier 78 provides an interval timer or counter that determines the R-R interval and verifies that the R-R interval falls within a predetermined threshold value that corresponds to the periodic response of the incoming ECG-suitable signal. Accordingly, the R-R interval verifier 78 minimizes or eliminates mistakes in identification of the R-wave and R-R intervals. For example, the R-R interval verifier 78 can filter out the amplitude of a T-wave from being mistaken for an R-wave by identifying the occurrence of the T-wave as being too close in time to the preceding R-wave. It will be appreciated that, although the R-R interval is used herein, various other heart rate timing indicators or intervals may be utilized, as desired for a given application.

Figure 14:
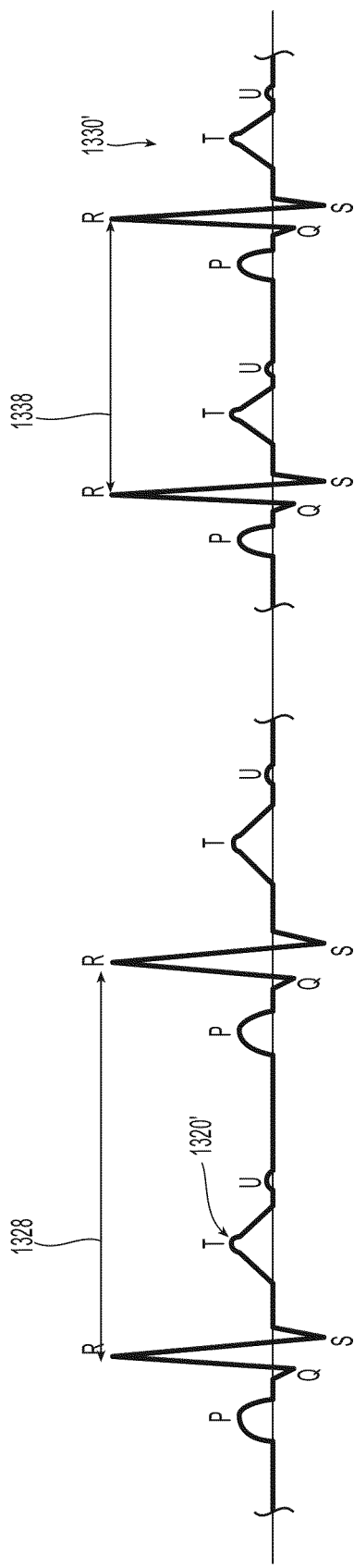
FIG. 14 is another illustrative view of an ECG waveform response in a subject patient to a vagus nerve stimulation treatment, according to an exemplary embodiment.

With each R-wave and R-R interval identified within the ECG waveform or equivalent, the computer processing device 50 determines one or more heart rate dynamics for assessment of the delivered stimulation signal. In some instances, the heart rate calculator 82 (shown in FIG. 6) may determine an instantaneous heart rate ("IHR") between adjacent R-waves at step 1020. For example, shown in FIG. 14 are adjacent R-waves in each of the ON period portion 1320' and the OFF period 1330' of the illustrative ECG waveform with respective determined R-R intervals (1328, 1338). Thus, in accordance with step 1020 of the process 1000 of FIG. 10, for each R-R interval, the IHR in beats per minute ("bpm") is determined by the following:

$$IHR = 1 \text{ beat}/(R\text{-}R \text{ interval msec}) \times (1000 \text{ msec/sec}) \times (60 \text{ sec/min})$$

From the IHR, several statistical aspects of the heart rate can also be determined by the heart rate calculator 82. In some embodiments, the real-time heart rate can be determined at step 1022 by taking a beat-to-beat average over a range of the latest recorded number of beats. For example, the real-time heart rate ("RTHR") can be determined by the average of the last five or fewer instantaneous heart rates. In some embodiments, the RTHR can be determined in step 1022 of the process 1000 by the average of the last three instantaneous heart rates in a manner as follows:

$$RTHR = [IHR(N) + IHR(N-1) + IHR(N-2)]/3,$$ where N is the most recent IHR value, where N−1 is an IHR value preceding the N value in time, and where N−2 is an IHR value preceding the N−1 value in time.

As can be appreciated, the IHR values can be qualified values that meet a threshold level of data quality, with inaccurate or inconsistent IHR values being disregarded, discounted, weighted, or modified to improve the quality of the IHR values used in the determination of the RTHR value. As can also be appreciated, the IHR(N), IHR(N−1), and IHR(N−2) values can be ordered in time in a sequence with each value being adjacent to the next in time, ordered in time in a sequence with unqualified IHR values interposed between qualified IHR values, and/or ordered in time in a sequence with a skipped IHR value or values interposed between qualified IHR values. The RTHR may also be displayed (e.g., via the display 58) at step 1022.

In a continuous manner, the storage memory 56b, in coordination with the R-R interval detector 70, stores in one or more data arrays each IHR, associated verified R-R interval, associated status identifier as either ON period or OFF period, and associated cycle number in the number of cycles defining the stimulus treatment. Accordingly, the heart rate calculator 82 determines, in real-time, the mean heart rate for each ON period of stimulation signal delivery and OFF period of rest in a given treatment cycle in steps 1024, 1026, respectively, of the process 1000. For example, where a stimulation signal cycle is defined by a 14 second ON period and a 66 second OFF period, the heart rate calculator 82 takes the cumulative average of most or all the IHRs over the 14 second ON period to determine the ON period mean heart rate ("(MHR)ON"). To determine the OFF period mean heart rate ("(MHR)OFF"), the heart rate calculator 82 takes the cumulative average of most or all IHRs over the 66 second OFF period. In one embodiment, the IHR values corresponding to the ON period and/or the OFF period can be qualified to eliminate low-quality IHR values or to eliminate IHR values that overlap or are proximate to the start or cessation of stimulation.

Additionally or alternatively to taking the cumulative average of all determined instantaneous heart rates to calculate mean heart rates, the heart rate calculator 82 can apply a data quality process that prefers, uses, or takes the cumulative average of the instantaneous heart rates within 25% of the mean of instantaneous heart rates for a given ON period or OFF period. Thus, the heart rate calculator 82 eliminates extremes in instantaneous heart rates in each of the ON period and OFF period by defining the minimum instantaneous heart rate at 25% below the mean and defining the maximum instantaneous heart rate at 25% above the mean. The heart rate calculator 82 can then determine the mean heart rate ("MHR") by taking the cumulative average of instantaneous heart rates falling between the maximum and minimums. The mean heart rate may also be displayed for the ON period and OFF period at steps 1024, 1026, respectively.

In step 1028 of process 1000, the heart rate calculator 82 determines (e.g., in real-time) the extent of bradycardia response. For example, the heart rate calculator 82 determines a heart rate reduction response for each cycle of treatment by determining the difference between the cumulative averages of the instantaneous heart rates to indicate a heart rate reduction ("HRR") as follows:

$$HRR = (MHR)OFF - (MHR)ON$$

A positive HRR indicates a bradycardia response and a negative HRR indicates a tachycardia response. A positive HRR reduction of less than 5% from the mean heart rate for the OFF period ((MHR)OFF) indicates a desired response of autonomic engagement (e.g., a response within the neural fulcrum zone). Accordingly, the HRR may provide an indication of the degree of autonomic engagement achieved by the stimulation intensity parameters being applied by the neurostimulator 22 to the vagus nerve. The HRR may also be displayed at step 1028.

Given the data compiled and collected by the computer processing device 50, the waveform generator 86 of the ECG processor 80 can further display a digital replica of the ECG waveform 1810, at step 1050, in the display 58 in real-time, as shown, for example, in FIG. 18. The ECG replica 1810 includes all the PQRSTU intervals of the waveform to provide a visual indicator to the subject patient, clinician, and/or physician of any possible arrhythmia to accompany the assessment indicators previously described. Moreover, the display 58 can display back to the subject patient or clinician each of the determined values from the assessment processes previously described. For example, the display 58 can report back the real-time heart rate (RTHR), the mean heart rates for each of the OFF period and ON period ((MHR)OFF, (MHR)ON), and the Heart Rate Reduction (HRR). Additionally, in some embodiments, the display 58 can show the R-wave axis and/or mark the R-wave intervals for the subject patient or clinician at steps 1052 and 1054.

Figure 15:
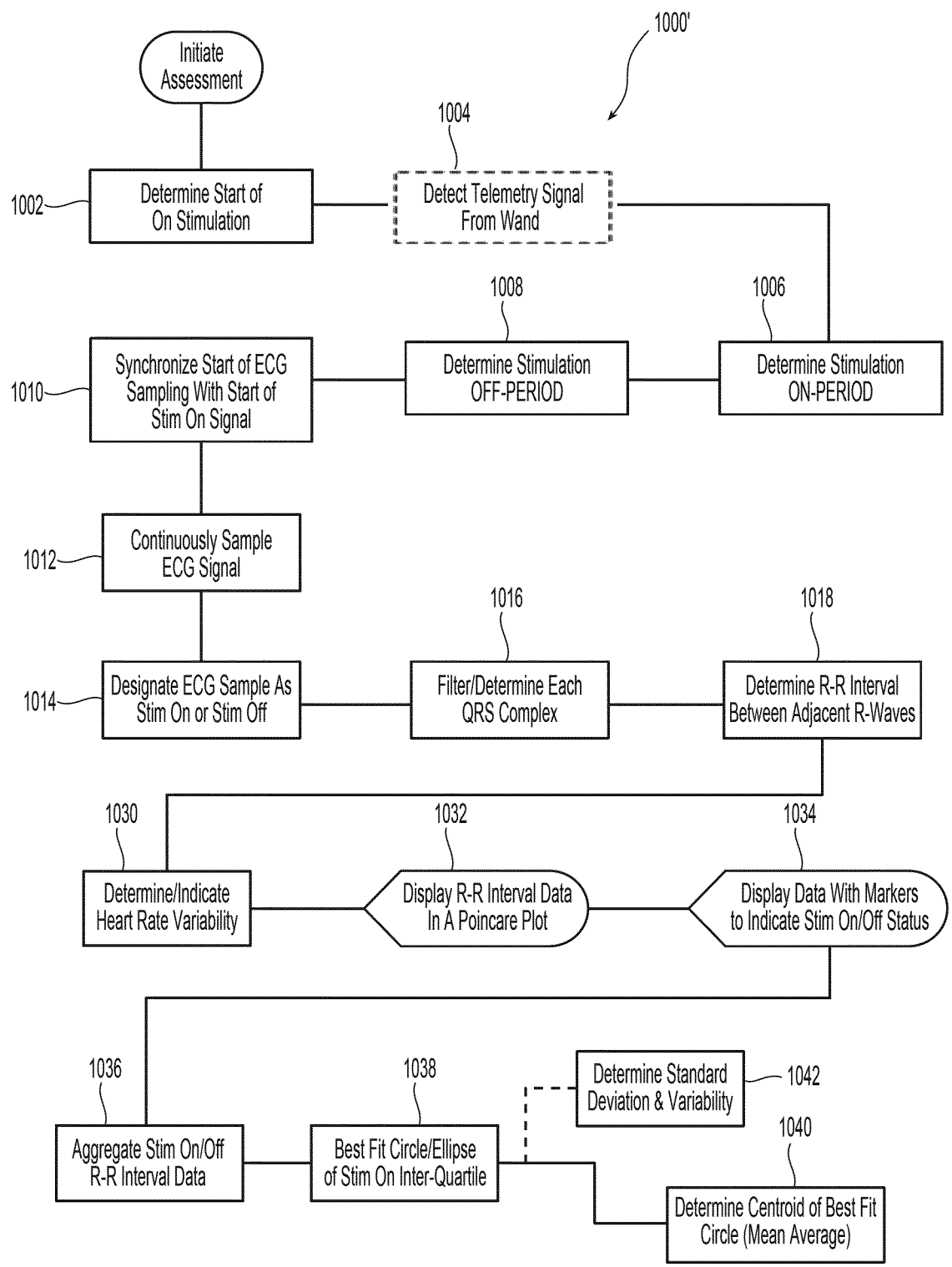
FIG. 15 is another embodiment of a method for assessing autonomic engagement response to vagus nerve stimulation therapy using the system of FIG. 2A, according to an exemplary embodiment.

Referring now to FIG. 15, a modified assessment method 1000' is shown. The modified assessment method 1000' is similar to the assessment method 1000 discussed above, and includes several identical method steps (e.g., steps 1002-1018). It should be appreciated that these assessment methods 1000, 1000' may be combined or otherwise performed together to provide additional information to the subject patient or clinician, as desired for a given application. According to the modified assessment method 1000', after the QRS complexes have been filtered and/or determined, at step 1016 and the R-R intervals between the adjacent R-waves have been determined, at step 1018, the heart rate variability is graphically displayed in a display step 1032 that provides the subject patient SP or clinician with a real-time indicator of autonomic engagement response to a delivered stimulus.

In particular, the variability calculator 84 determines a difference in the heart rate variability response between the ON period and the OFF period. In an aspect, the storage memory 56b, in coordination with the ECG processor 80 and variability calculator 84, stores in one or more data arrays the R-R interval for each preceding R-R interval and stimulation status ON/OFF period for a number of cycles in the stimulation treatment. Accordingly, the stored data array can be defined as {R-R Interval(N+1), R-R Interval(N), ON/OFF period Status, #Cycle}. The data can be aggregated for each cycle in a manner that differentiates ON period of stimulation signal delivery and OFF period of resting period. In some embodiments, for each cycle, the mean average of all the R-R Intervals for the ON period and the mean average of all the R-R Intervals for the OFF period are determined and compared. A separation in the mean average can be used to show an autonomic engagement response to the delivery of vagus nerve stimulation treatment.

Figure 16:
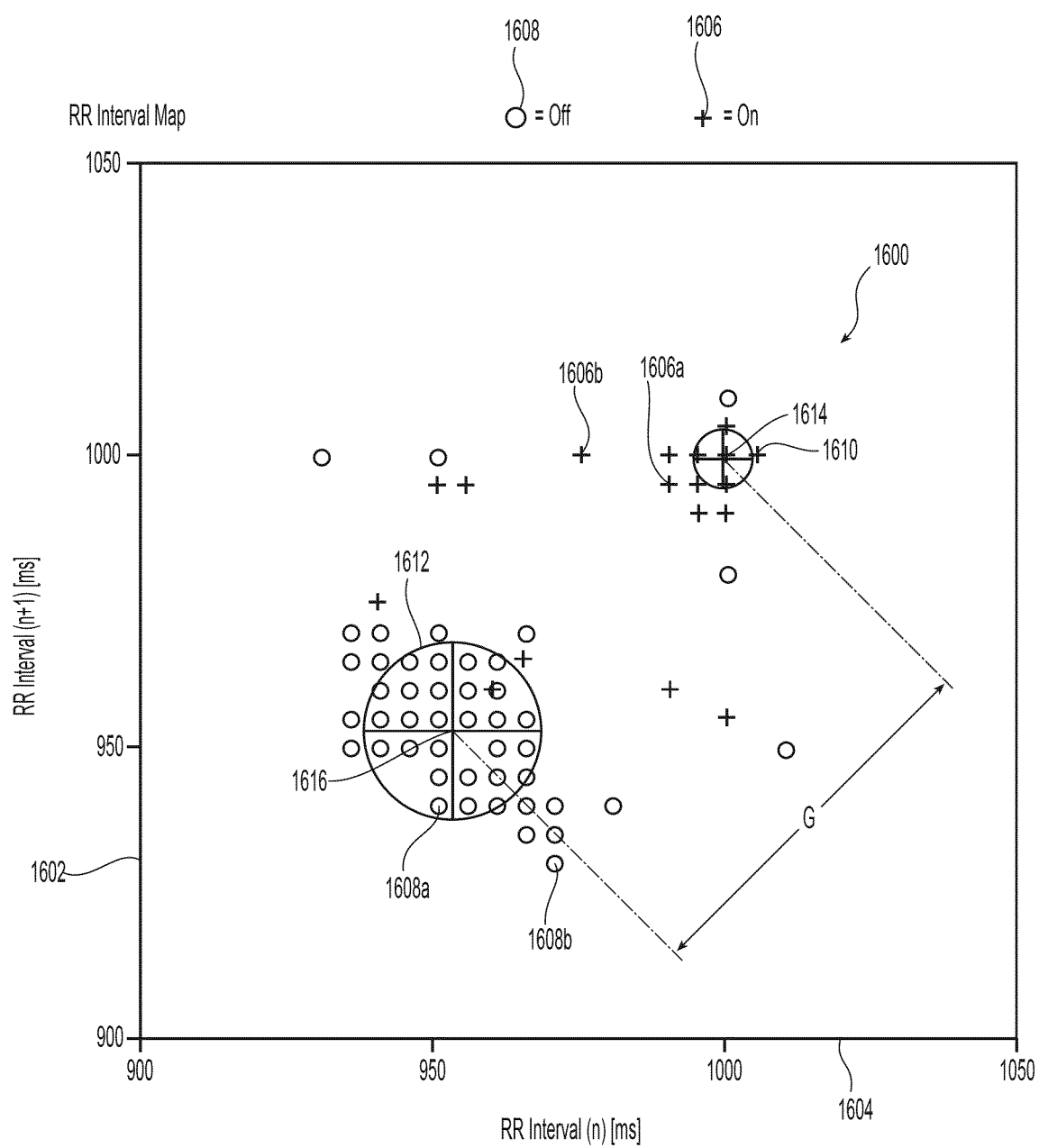
FIG. 16 is an illustrative view of a Poincare plot display generated from the method of FIG. 15, according to an exemplary embodiment.

More particularly, the R-R interval differential between the ON period and OFF period is displayed in a Poincaré plot 1600 as illustrated in FIG. 16. The display can be generated (e.g., in real-time) for the subject patient SP or clinician to view at the display 58 of the system 10. The plot shows the R-R interval (R-R Interval(N+1)) along the vertical axis 1602 in msec, as a function of the preceding R-R interval (R-R Interval(N)) along the horizontal axis 1604 in msec. In step 1034 of the process 1000', the R-R intervals for the ON period and OFF period are distinguished from one another by differentiating markers, as shown in FIG. 16. R-R interval values for the ON period are shown with "+" markers 1606, and the OFF period values are shown with "O" markers 1608. In accordance with an aggregating step 1036 of the process 1000', the plot 1600 further provides a visual indication of autonomic engagement as determined by the separation or gap G between the cluster of ON period R-R interval values from the cluster of OFF period R-R interval values.

In another process step 1038, the plot 1600 shows a first best-fit circle 1610 about the R-R interval ON period data (e.g., 1606a, 1606b) and a second best-fit circle 1612 about the R-R interval OFF period data (e.g., 1608a. 1608b). The best-fit circles 1610, 1612 are defined by a radius about the centroids 1614, 1616, which are determined by the respective means of the ON period and OFF period R-R interval data at step 1040. The radii of the best-fit circles 1610, 1612 are calculated or defined by a minimum and maximum in the R-R interval values about the mean. In some embodiments, the heart rate variability calculator 84 determines the 25th quartile and the 75th quartile of the R-R interval values and determines the mean of values falling between the 25th and the 75th quartiles about which to determine the best fit circles. The gap G is defined as the straight line distance between the centroids 1614, 1616 to indicate an extent of autonomic engagement. Alternatively, the heart rate variability calculator 84 defines the minimum R-R interval value at 25% below the mean and defines the maximum R-R interval value at 25% above the mean. In another alternative, the best-fit circles 1610, 1612 include or circumscribe each of the minimum and maximum values.

Figure 17:
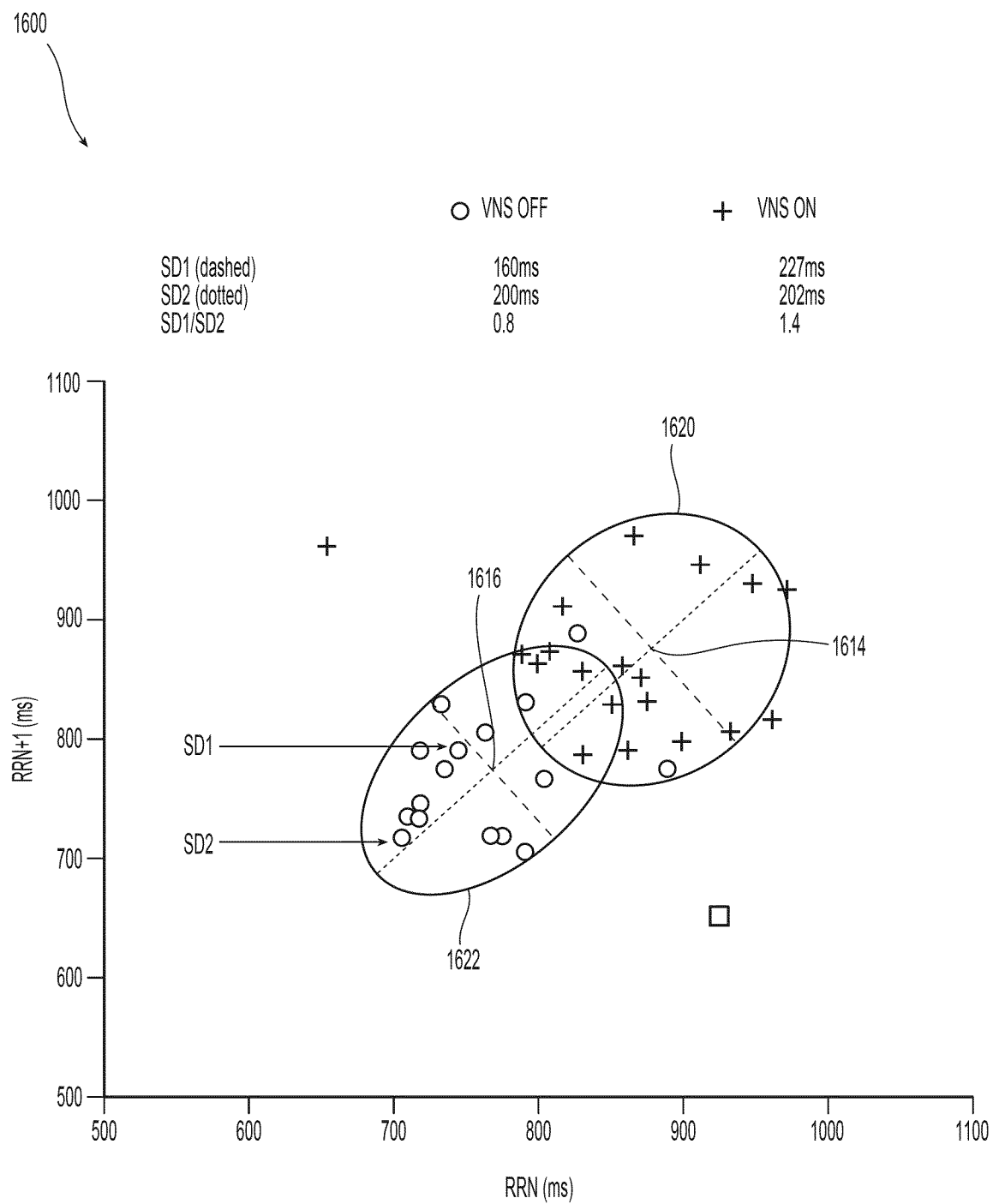
FIG. 17 is an illustrative view of another Poincare plot display generated from the method of FIG. 15, according to an exemplary embodiment.

Shown in FIG. 17 is another exemplary set of graphical indicators in a plot 1600' indicating heart rate variability response to the vagus nerve stimulation treatment. The heart rate variability calculator 84 can determine and aggregate, as alternatively provided in step 1038 of the process 1000' of FIG. 15, the R-R interval data to best-fit ellipses 1620, 1622 for each of the ON period and OFF period data to indicate the extent of heart rate variability within each respective period during stimulation delivery and during the resting period. The variability calculator 84 can determine each of the major axis SD2 and the minor axis SD1 for each of the ellipses 1620, 1622 as part of determining standard deviation and variability at step 1042 of the process 1000'. In some embodiments, the minor axis SD1 is determined as reflecting the standard deviation of the IHR about the mean, and the major axis SD2 is determined as the standard deviation of the continuous heart rate about the mean. The major axis SD2 can be found by a best fit to the data with the axis SD2 passing through the centroid or mean 1614, 1616 of the R-R interval. The minor axis SD1 extends transverse to the major axis SD2 and passes through the centroid 1614, 1616. Accordingly, the ellipse 1620, 1622 is a best fit that is centered about the centroid 1614, 1616, respectively, and passes through the axes SD2, SD1 while encompassing the data disposed about the respective centroid 1614, 1616.

Accordingly, the systems and methods described herein allow for the determination of a stimulation delivery schedule of the stimulation provided by the neurostimulator 22 to the vagus nerve of the patient. Monitored ECG data taken from the patient may then be synchronized with the stimulation ON periods and the stimulation OFF periods of the stimulation and used by physicians to analyze various aspects of the neurostimulation treatment provided to the patient. For example, in some instances, the physician or clinician may be provided with a degree of autonomic engagement (e.g., a heart rate reduction) achieved by a given set of stimulation intensity parameters provided to the patient during treatment. If the degree of autonomic engagement is not within the neural fulcrum zone, the physician or clinician may make iterative adjustments to the stimulation intensity parameters delivered by the neurostimulator 22 based on the determined degree of autonomic engagement for each set of stimulation intensity parameters. For example, for each subsequent set of stimulation intensity parameters, the physician or clinician may compare the degree of autonomic engagement achieved to the degree of autonomic engagement achieved by the previous set of stimulation intensity parameters to determine whether the adjustments made successfully increased the degree of autonomic engagement toward the neural fulcrum zone. Accordingly, by making iterative adjustments to the stimulation intensity parameters and continuously monitoring the degree of autonomic engagement achieved by each set of stimulation intensity parameters, the physician or clinician may gradually achieve or identify a stimulation signal that elicits a cardiac response within the neural fulcrum zone, thereby improving the efficacy of the neurostimulation therapy.

While embodiments been particularly shown and described, those skilled in the art will understand that the foregoing and other changes in form and detail may be made therein without departing from the spirit and scope. For example, in various embodiments described above, the stimulation is applied to the vagus nerve. Alternatively, spinal cord stimulation (SCS) may be used in place of or in addition to vagus nerve stimulation for the above-described therapies. SCS may utilize stimulating electrodes implanted in the epidural space, an electrical pulse generator implanted in the lower abdominal area or gluteal region, and conducting wires coupling the stimulating electrodes to the generator.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z. Thus, such conjunctive language is not generally intended to imply that certain embodiments require at least one of X, at least one of Y, and at least one of Z to each be present.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed:

1. A neurostimulation system comprising:
   a sensor configured to detect a cardiac physiological measure of a patient;
   a control system programmed to:
      receive one or more stimulation timing parameters of a treatment;
      monitor, via the sensor, the cardiac physiological measure during the treatment;
      detect a first change and a second change in the cardiac physiological measure during the treatment;
      compare a time period between the first change and the second change with the one or more stimulation timing parameters; and
      determine, based on the comparison, a first transition time in a duty cycle of a neurostimulation signal delivered to the patient where the neurostimulation signal transitions between a stimulation OFF period and a stimulation ON period.

2. The neurostimulation system of claim 1, wherein the one or more stimulation timing parameters comprise one or more of a stimulation ON period duration, a stimulation OFF period duration, or an overall stimulation cycle duration, and the control system is further programmed to:
   determine the stimulation ON period and the stimulation OFF period based on the one or more stimulation timing parameters and the first transition time in the duty cycle where the neurostimulation signal transitions between the stimulation OFF period and the stimulation ON period.

3. The neurostimulation system of claim 2, wherein the control system is further programmed to:
   record the cardiac physiological measure during the stimulation ON period and the stimulation OFF period during the treatment at a first set of stimulation intensity parameters of the neurostimulation signal;
   compare the cardiac physiological measure recorded during the stimulation ON period to the cardiac physiological measure recorded during the stimulation OFF period for the first set of stimulation intensity parameters; and
   determine a first magnitude of stimulation-induced change of the cardiac physiological measure for the first set of stimulation intensity parameters based on the comparison of the cardiac physiological measure recorded during the stimulation ON period to the cardiac physiological measure recorded during the stimulation OFF period.

4. The neurostimulation system of claim 3, wherein the control system is further programmed to:
   determine a first degree of autonomic engagement for the first set of stimulation intensity parameters based on the first magnitude of stimulation-induced change;
   determine that the first degree of autonomic engagement for the first set of stimulation intensity parameters is not within a neural fulcrum zone; and responsive to the determination that the first degree of autonomic engagement is not within the neural fulcrum zone, identify a second set of stimulation intensity parameters of the neurostimulation signal based on the first degree of autonomic engagement, the second set of stimulation intensity parameters being different than the first set of stimulation intensity parameters.

5. The neurostimulation system of claim 1, wherein the cardiac physiological measure is at least one of a heart rate, an R-R interval, a P-R interval, a Q-T interval, or a heart rate variability of the patient.

6. The neurostimulation system of claim 5, wherein one of the first change or the second change in the cardiac physiological measure during the treatment is a reduction of the heart rate of between one and five beats per minute.

7. The neurostimulation system of claim 1, further comprising an implantable medical device (IMD) configured to deliver the treatment to the patient, the IMD comprising a neurostimulator coupled to an electrode assembly, the neurostimulator including an implantable pulse generator configured to generate the neurostimulation signal delivered to the patient via the electrode assembly.

8. A method of delivering a neurostimulation signal to a patient from an implantable pulse generator, the method comprising:
receiving, by a control system, one or more stimulation timing parameters of a treatment;
delivering, by the implantable pulse generator, the neurostimulation signal to the patient via an electrode assembly, the neurostimulation signal having a duty cycle with a stimulation ON period and a stimulation OFF period;
detecting, by a sensor, a cardiac physiological measure of the patient;
monitoring, by the control system, the cardiac physiological measure during the treatment via the sensor;
detecting, by the control system, a first change and a second change in the cardiac physiological measure during the treatment;
comparing, by the control system, a time period between the first change and the second change with the one or more stimulation timing parameters; and
determining, by the control system based on the comparison, a first transition time in the duty cycle where the neurostimulation signal transitions between the stimulation OFF period and the stimulation ON period.

9. The method of claim 8, wherein the one or more stimulation timing parameters comprise one or more of a stimulation ON period duration, a stimulation OFF period duration, or an overall stimulation cycle during, the method further comprising:
determining, by the control system, the stimulation ON period and the stimulation OFF period based on the one or more stimulation timing parameters and the first transition time in the duty cycle where the neurostimulation signal transitions between the stimulation OFF period and the stimulation ON period.

10. The method of claim 9, further comprising:
recording, by the control system, the cardiac physiological measure during the stimulation ON period and the stimulation OFF period during the treatment at a first set of stimulation intensity parameters of the neurostimulation signal;
comparing, by the control system, the cardiac physiological measure recorded during the stimulation ON period to the cardiac physiological measure recorded during the stimulation OFF period for the first set of stimulation intensity parameters; and
determining, by the control system, a first magnitude of stimulation-induced change of the cardiac physiological measure for the first set of stimulation intensity parameters based on the comparison of the cardiac physiological measure recorded during the stimulation ON period to the cardiac physiological measure recorded during the stimulation OFF period.

11. The method of claim 10, further comprising:
determining, by the control system, a first degree of autonomic engagement for the first set of stimulation intensity parameters based on the first magnitude of stimulation- induced change;
determining, by the control system, that the first degree of autonomic engagement for the first set of stimulation intensity parameters is not within a neural fulcrum zone; and
responsive to the determination that the first degree of autonomic engagement is not within the neural fulcrum zone, identifying, by the control system, a second set of stimulation intensity parameters of the neurostimulation signal based on the first degree of autonomic engagement, the second set of stimulation intensity parameters being different than the first set of stimulation intensity parameters.

12. The method of claim 11, further comprising:
delivering, by the implantable pulse generator, the neurostimulation signal having the second set of stimulation intensity parameters to the patient via the electrode assembly;
recording, by the control system, the cardiac physiological measure during the stimulation ON period and the stimulation OFF period during the treatment at the second set of stimulation intensity parameters of the neurostimulation signal;
comparing, by the control system, the cardiac physiological measure recorded during the stimulation ON period to the cardiac physiological measure recorded during the stimulation OFF period for the second set of stimulation intensity parameters;
determining, by the control system, a second magnitude of stimulation-induced change of the cardiac physiological measure for the second set of stimulation intensity parameters based on the comparison of the cardiac physiological measure recorded during the stimulation ON period to the cardiac physiological measure recorded during the stimulation OFF period for the second set of stimulation intensity parameters;
determining, by the control system, a second degree of autonomic engagement for the second set of stimulation intensity parameters based on the second magnitude of stimulation-induced change; and
comparing, by the control system, the first degree of autonomic engagement to the second degree of autonomic engagement.

13. The method of claim 12, wherein a plurality of degrees of autonomic engagements are determined iteratively for a plurality of sets of stimulation intensity parameters until a degree of autonomic engagement is within the neural fulcrum zone, the plurality of degrees of autonomic engagements including at least the first degree of autonomic engagement and the second degree of autonomic engagement, and the plurality of sets of stimulation intensity parameters including at least the first set of stimulation intensity parameters and the second set of stimulation intensity parameters.

14. The method of claim 8, wherein the first transition time in the duty cycle is where the neurostimulation signal transitions from the stimulation OFF period to the stimulation ON period and the method further comprises:
  determining, by the control system, a second transition time in the duty cycle where the neurostimulation signal transitions from the stimulation ON period to the stimulation OFF period based on the second change in the cardiac physiological measure.

15. The method of claim 8, wherein the cardiac physiological measure is at least one of an R-R interval, a P-R interval, a Q-T interval, or a heart rate variability of the patient.

16. One or more non-transitory computer-readable mediums comprising instructions executable by one or more processors to:
  receive one or more stimulation timing parameters of a treatment
  detect, via a sensor, a cardiac physiological measure of a patient;
  monitor, via the sensor, the cardiac physiological measure during the treatment
  detect a first change and a second change in the cardiac physiological measure during the treatment;
  compare a time period between the first change and the second change with the one or more stimulation timing parameters; and
  determine, based on the comparison, a first transition time in a duty cycle of a neurostimulation signal delivered to the patient where the neurostimulation signal transitions between a stimulation OFF period and a stimulation ON period.

17. The one or more non-transitory computer-readable mediums of claim 16, wherein the one or more stimulation timing parameters, comprise one or more of a stimulation ON period duration, a stimulation OFF period duration, or an overall stimulation cycle duration, and the instructions are further executable by the one or more processors to:
  deliver, via an implantable pulse generator, the neurostimulation signal to the patient via an electrode assembly; and
  determine the stimulation ON period and the stimulation OFF period based on the one or more stimulation timing parameters and the first transition time in the duty cycle where the neurostimulation signal transitions between the stimulation OFF period and the stimulation ON period.

18. The one or more non-transitory computer-readable mediums of claim 17, wherein the instructions are further executable by the one or more processors to:
  record the cardiac physiological measure during the stimulation ON period and the stimulation OFF period during the treatment at a first set of stimulation intensity parameters of the neurostimulation signal;
  compare the cardiac physiological measure recorded during the stimulation ON period to the cardiac physiological measure recorded during the stimulation OFF period for the first set of stimulation intensity parameters; and
  determine a first magnitude of stimulation-induced change of the cardiac physiological measure for the first set of stimulation intensity parameters based on the comparison of the cardiac physiological measure recorded during the stimulation ON period to the cardiac physiological measure recorded during the stimulation OFF period.

19. The one or more non-transitory computer-readable mediums of claim 18, wherein the instructions are further executable by the one or more processors to:
  determine a first degree of autonomic engagement for the first set of stimulation intensity parameters based on the first magnitude of stimulation-induced change;
  determine that the first degree of autonomic engagement for the first set of stimulation intensity parameters is not within a neural fulcrum zone; and
  responsive to the determination that the first degree of autonomic engagement is not within the neural fulcrum zone, identify a second set of stimulation intensity parameters of the neurostimulation signal based on the first degree of autonomic engagement, the second set of stimulation intensity parameters being different than the first set of stimulation intensity parameters.

20. The one or more non-transitory computer-readable mediums of claim 16, wherein the cardiac physiological measure is at least one of an R-R interval, a P-R interval, a Q-T interval, or a heart rate variability of the patient.

* * * * *